(12) United States Patent
Sanghani

(10) Patent No.: US 9,198,909 B1
(45) Date of Patent: Dec. 1, 2015

(54) MATERIALS AND METHODS FOR INHIBITING MAMALIAN S-NITROSOGLUTATHIONE REDUCTASE

(75) Inventor: Paresh Sanghani, Westfield, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 734 days.

(21) Appl. No.: 12/813,721

(22) Filed: Jun. 11, 2010

Related U.S. Application Data

(63) Continuation of application No. PCT/US2008/008673, filed on Dec. 13, 7008.

(60) Provisional application No. 61/013,522, filed on Dec. 13, 2007, provisional application No. 61/021,781, filed on Jan. 17, 2008.

(51) Int. Cl.
| | | |
|---|---|---|
| *A61K 31/519* | (2006.01) | |
| *A61K 31/402* | (2006.01) | |
| *A61K 31/404* | (2006.01) | |

(52) U.S. Cl.
CPC ............. *A61K 31/519* (2013.01); *A61K 31/402* (2013.01); *A61K 31/404* (2013.01)

(58) Field of Classification Search
CPC .. A61K 31/519; A61K 31/402; A61K 31/404
See application file for complete search history.

(56) References Cited

U.S. PATENT DOCUMENTS

| | | | |
|---|---|---|---|
| 4,792,568 | A | 12/1988 | Auerbach |
| 5,137,910 | A | 8/1992 | Gray et al. |
| 5,229,413 | A | 7/1993 | Gray et al. |
| 2005/0014697 | A1 | 1/2005 | Stamler et al. |
| 2007/0135454 | A1 * | 6/2007 | Bayliss et al. ............. 514/260.1 |

FOREIGN PATENT DOCUMENTS

| | | | |
|---|---|---|---|
| WO | WO 02/055018 A2 | | 7/2002 |
| WO | WO-2005/049613 A1 * | | 6/2005 |
| WO | WO 2008/113747 A1 | | 9/2008 |
| WO | WO 2008/121836 A1 | | 10/2008 |

OTHER PUBLICATIONS

Green et al. Biochemistry, 2012, vol. 51, pp. 2157-2168.*
Ivachtchenko et al. 2004, J. Comb. Chem., 6, 573-583.*
Basu et al., The DNA-dependent protein kinase participates in the activation of NF kappa B following DNA damage, *Biochem. Biophys. Res. Commun.*, 247(1):79-83 (1998).
Blonder et al., Oral S-Nitrosoglutathione reductase inhibitors attenuate pulmonary inflammation and decrease airspace enlargement in experimental models of chronic obstructive pulmonary disease, (2011).
Blonder et al., Small molecule inhibitors of GSNOR possess anti-inflammatory and bronchodilatory actions in mouse models of inflammatory lung disease and modulate CFTR function in F508del-CFTR Mice, (2013).
Blonder et al., S-nitrosoglutathione reductase inhibitors for the prevention and treatment of experimental colitis, *Inflammatory Bowel Diseases*,17:S86 (2011).
Chandel et al., Role of oxidants in NF-kappa B activation and TNF-alpha gene transcription induced by hypoxia and endotoxin, *J. Immunol.*, 165(2):1013-21 (2000).
Childers et al., A new model of cystic fibrosis pathology: lack of transport of glutathione and its thiocyanate conjugates, *Med. Hypotheses*, 68:101-12 (2007).
Ferrini et al., S-Nitrosoglutathione Reductase Inhibition Regulates Allergen-Induced Lung Inflammation and Airway Hyperreactivity, *PLoS One*, 8(7):e70351 (2013).
Fitzgerald et al., Tumour necrosis factor-alpha (TNF-alpha) increases nuclear factor kappaB (NFkappaB) activity in and interleukin-8 (IL-8) release from bovine mammary epithelial cells, *Vet. Immunol. Immunopathol.*, 116(1-2):59-68 (2007).
Kelleher et al., NOS2 regulation of NF-kappaB by S-nitrosylation of p65, *J. Biol. Chem.*, 282:30667-72 (2007).
Liu et al., A metabolic enzyme for S-nitrosothiol conserved from bacteria to humans, *Nature*, 410:490-4 (2001).
Liu et al., Essential roles of S-nitrosothiols in vascular homeostasis and endotoxic shock, *Cell*, 116:617-28 (2004).
Qin et al., LPS induces CD40 gene expression through the activation of NF-kappaB and STAT-1alpha in macrophages and microglia, *Blood*, 106(9):3114-22 (2005).
Que et al., Protection from experimental asthma by an endogenous bronchodilator, *Science*, 308:1618-21 (2005).
Que et al., Systemic and/or Local Aerosol Inhibition of S-Nitrosoglutathione Reductase (GSNOR) Ameliorates Physiologic, Biologic, and Proteomic Phenotypes in an Allergic Mouse Model of Inflammatory Airway Disease, (2011).
Sanghani et al., Kinetic and Cellular Characterization of Novel Inhibitors of S-Nitrosoglutathione Reductase, *J. Biol. Chem.*, 284(36):24354-62 (2009).
Zeitlin, Is it go or NO go for S-nitrosylation modification-based therapies of cystic fibrosis transmembrane regulator trafficking, *Mol. Pharmacol.*, 70:1155-8 (2006).
Database Registry [Online] Chemical Abstracts Service, Columbus, Ohio, US; Jun. 2, 2804 (Jun. 2, 2004), XP002693086, retrieved from STN Database accession No. 688347-51-5.

* cited by examiner

*Primary Examiner* — Kara R McMillian
(74) *Attorney, Agent, or Firm* — Faegre Baker Daniels LLP

(57) ABSTRACT

The current study reports novel inhibitors of s-nitrosoglutathione reductase (GSNOR) identified that specifically inhibit GSNOR among the alcohol dehydrogenases. These inhibitors may bind into the GSNO binding site and inhibit GSNOR at multiple places in its kinetic pathway. These molecules inhibit GSNOR in a dose dependent manner and demonstrate that GSNOR actively regulates the s-nitrosylation of proteins against incoming low molecular weight nitrosothiols. These compounds are useful in method of treatment of diseases such as asthma, chronic obstructive pulmonary disease, heart disease, heart failure, heart attack, hypertension, atherosclerosis, restenosis, impotence, Parkinson's disease, Alzheimer's disease, amyotrophic lateral sclerosis, stroke, septic shock, cardiogenic shock, endotoxic shock, toxic shock syndrome, systemic inflammatory response syndrome, and other inflammatory diseases. These compounds can also be used to diagnose and/or study disease and/or conditions or enzymes involving the s-nitrosylation of proteins.

4 Claims, 27 Drawing Sheets

Table 1 Structures of FDH inhibitors

| Compound No. | Structures | % inhibition | | IC$_{50}$ at pH 7.5 (μM) |
|---|---|---|---|---|
| | | pH 10 | pH 7.5 | |
| Dodecanoic acid | CH$_3$(CH$_2$)$_{10}$COOH | 4 | 19 | 212 |
| 1 | 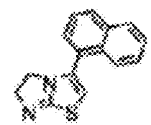 | 86 | 17 | ND |
| 2 | 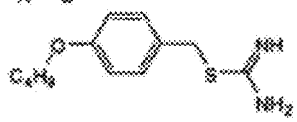 | 53 | 1.7 | ND |
| 3 | 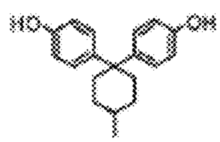 | 97 | 35 | 51 |
| 4 | 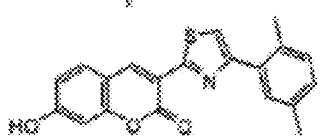 | 95 | 78 | 2.2* |
| 5 | 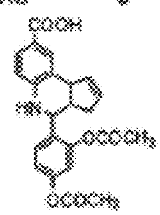 | 28 | 23 | |
| | | 76# | 78# | 2.1# |
| 6 | 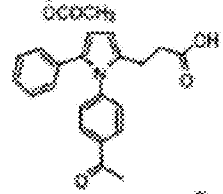 | 78 | 93 | 1.3 |
| 7 | 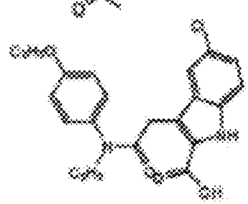 | 55 | 91 | 2.4 |
| 8 | 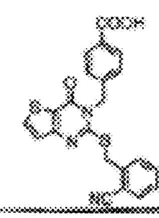 | 75 | 95 | 1.1 |

FIG. 7

Table 2 Inhibition of the alcohol dehydrogenase isozymes by GSNOR inhibitors

| Enzyme | % Inhibition[a] | | | | |
|---|---|---|---|---|---|
| | Compd 4 | Compd 5 | Compd 6 | Compd 7 | Compd 8 |
| GSNOR | 22 | 47 | 77 | 71 | 73 |
| $\beta_2\beta_2$-ADH | 6 | 8 | 5 | 0 | 5 |
| $\sigma\sigma$-ADH | 29 | 15 | 4 | 13 | 8 |
| $\pi$-ADH | 100 | 9 | 6 | 1 | 3 |

FIG. 8

Table 3. Mechanism of inhibition of GSNOR by GSNOR inhibitors[a]

| Compound | Varied Substrate | Type of inhibition | $K_{ia}$, μM | $K_{ii}$, μM | $K_D$, μM[b] |
|---|---|---|---|---|---|
| 6 | GSNO | NC | 1.7 ± 0.2 | 1.8 ± 0.1 | 1.3 ± 0.3 |
|   | NADH | UC |  | 1.5 ± 0.1 |  |
| 7 | GSNO | NC | 1.9 ± 0.2 | 4.0 ± 0.3 | 6.5 ± 1.0 |
|   | NADH | NC | 12 ± 5 | 2.5 ± 0.1 |  |
| 8 | GSNO | NC | 2.6 ± 0.3 | 1.6 ± 0.1 | 2.0 ± 0.1 |
|   | NADH | UC |  | 1.7 ± 0.1 |  |
| Dodecanoic acid | GSNO | NC | 280 ± 40 | 190 ± 10 |  |

FIG. 9

TABLE 4. Representative inhibitors of the enzyme: structure, compound number, percent inhibition; and comments.

| STRUCTURE | Compound Number | % Inhibition | Comments/ IC$_{50}$ μM |
|---|---|---|---|
| 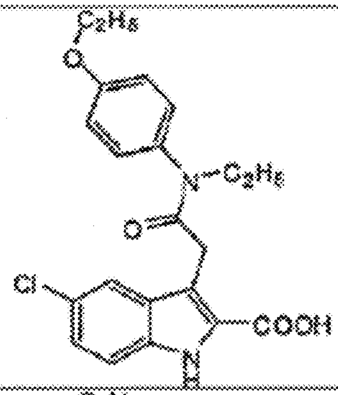 | 24 | 83 | |
| 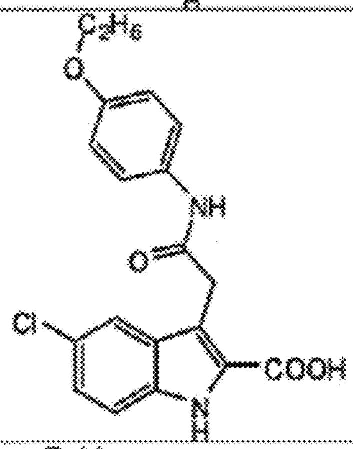 | 59 | 45 | |
| 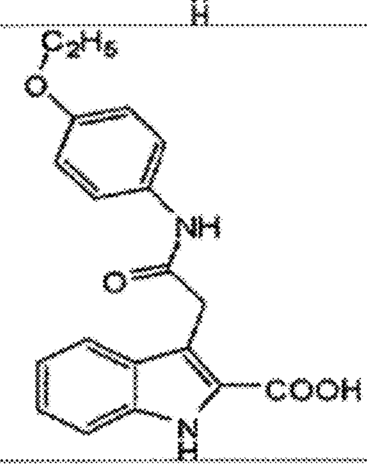 | 56 | 11 | |

TABLE 4 continued

| STRUCTURE | Compound Number | % Inhibition | Comments/ IC$_{50}$ μM |
|---|---|---|---|
| (5-Cl-indole-2-COOH with 3-CH$_2$-C(O)-N(C$_2$H$_5$)(2-OC$_2$H$_5$-phenyl)) | 63 | 55 | |
| (5-Cl-indole-2-COOH with 3-CH$_2$-C(O)-N(C$_2$H$_5$)$_2$) | 64 | 41 | |
| (5-Cl-indole-2-COOH with 3-CH$_2$-C(O)-N(C$_4$H$_9$)(C$_2$H$_5$)) and (5-Cl-indole-2-COOH with 3-CH$_2$-C(O)-N(C$_4$H$_9$)(CH$_3$)) | 60, 61 | 39, 26 | |

FIG. 10B

TABLE 4 continued

| STRUCTURE | Compound Number | % Inhibition | Comments/ IC₅₀, μM |
|---|---|---|---|
| (structure: 5-chloro-3-[2-(N-ethyl-N-(4-methoxyphenyl)amino)-2-oxoethyl]-1H-indole-2-carboxylic acid) | 69 | 55 | |
| (structure: 5-chloro-3-[2-(N-ethyl-N-(4-ethylphenyl)amino)-2-oxoethyl]-1H-indole-2-carboxylic acid) | 66 | 66 | |
| (structure: 5-chloro-3-[2-(N-ethyl-N-(4-fluorophenyl)amino)-2-oxoethyl]-1H-indole-2-carboxylic acid) | 67 | 49 | |

FIG. 10C

TABLE 4 continued

| STRUCTURE | Compound Number | % Inhibition | Comments/ IC₅₀ μM |
|---|---|---|---|
| (structure with H₃CO-phenyl, N-C₂H₅, indole-2-COOH) | 58 | 10 | |
| (structure with OC₂H₅ ester phenyl, NH, Cl-indole-2-COOH) | 71 | 62 | |
| (structure with C₂H₅O-phenyl, N-C₃H₇, Cl-indole-2-COOH) | 70 | 85 | |
| (pyrrole structure with R group) R=H | 12 | 93 | |
| R=CH₃ | 13 | 90 | |
| R=Br | 14 | 76 | |
| R=OCH₃ | | | |

FIG. 10D

TABLE 4 continued

| STRUCTURE | Compound Number | % Inhibition | Comments/ IC$_{50}$ µM |
|---|---|---|---|
| 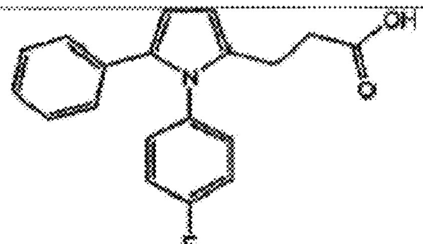 | 43 | 37 | |
| 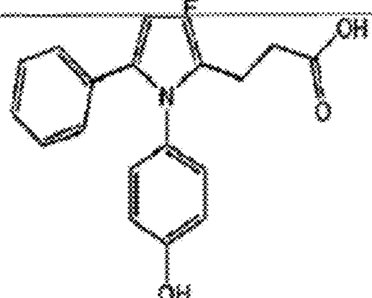 | 44 | 89 | 1.5 µM |
| 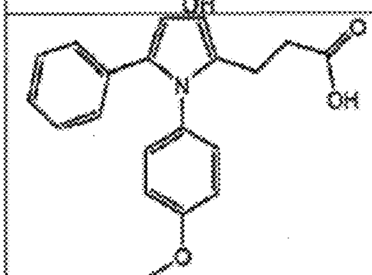 | 45 | 78 | 3.2 µM |
| 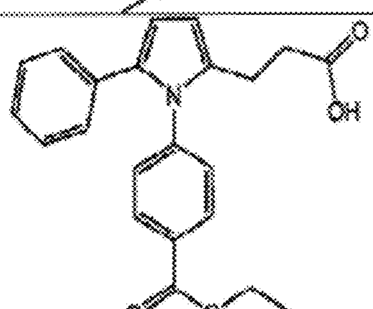 | 46 | 68 | |

TABLE 4 continued

| STRUCTURE | Compound Number | % Inhibition | Comments/ IC$_{50}$, µM |
|---|---|---|---|
| 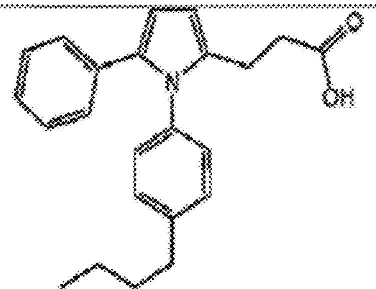 | 47 | 33 | |
| 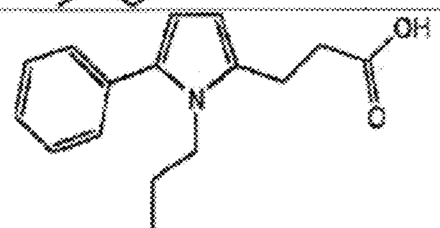 | 48 | 51 | 18 µM |
| 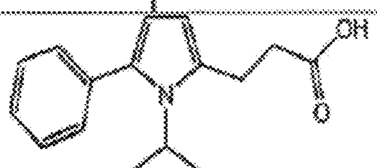 | 49 | 53 | 5.1 µM |
| 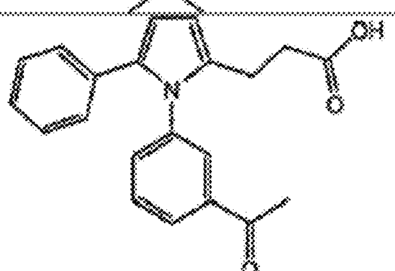 | 50 | 46 | |
| 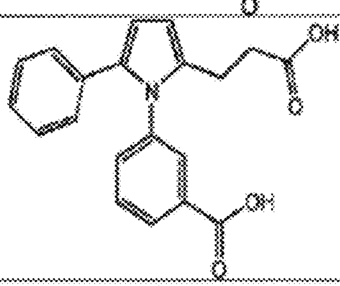 | 51 | 30 | |

TABLE 4 continued

| STRUCTURE | Compound Number | % Inhibition | Comments/ IC$_{50}$, μM |
|---|---|---|---|
| 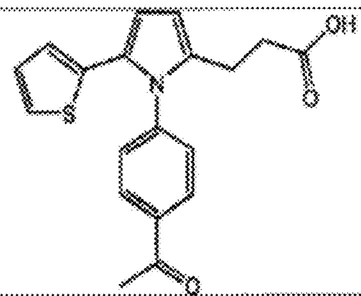 | 52 | 91 | 0.64 μM |
| 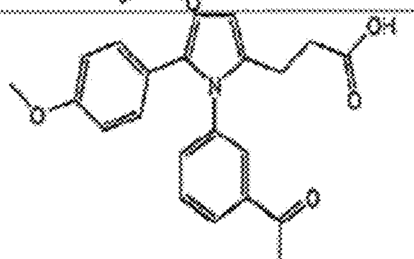 | 53 | 57 | 24 μM |
| 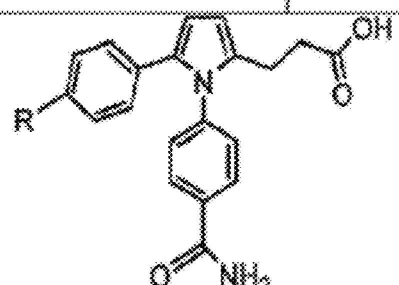 | R=H 72<br>R=OCH$_3$ 84<br>R=CH$_3$ 86 | 93<br>94 | 0.5 μM<br>0.2 μM |
| 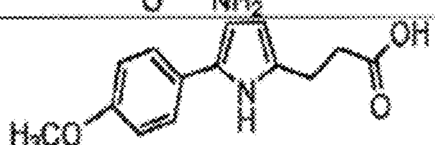 | 75 | 9.1 | |
| 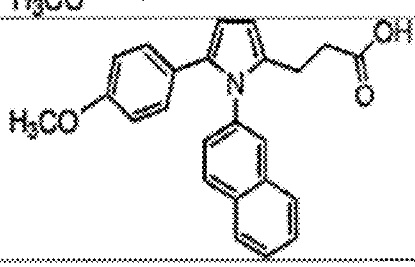 | 76 | 35 | |

TABLE 4 continued

| STRUCTURE | Compound Number | % Inhibition | Comments/ IC$_{50}$ µM |
|---|---|---|---|
| (structure) | 77 | 91 | 0.93 µM |
| (structure) | 78 | 71 | 5.6 µM |
| (structure) | 79 | 50 | 8.1 µM |
| (structure) | 80 | 46 | |
| (structure) | 81 | 4.4 | |

FIG. 10H

TABLE 4 continued

| STRUCTURE | Compound Number | % Inhibition | Comments/ IC$_{50}$ µM |
|---|---|---|---|
| (structure) | 82 | 33 | |
| (structure) | 83 | 11 | |

FIG. 10I

Scheme II – continued

MATERIALS AND METHODS FOR INHIBITING MAMALIAN S-NITROSOGLUTATHIONE REDUCTASE

CROSS-REFERENCE TO RELATED APPLICATION

This application is a continuation of PCT International Patent Application No. PCT/US08/86738 filed on Dec. 13, 2008, entitled "Materials and Methods for Inhibiting Mamalian S-Nitrosoglutathione Reductase," which claims the benefit under 35 U.S.C. §119 of U.S. Provisional Patent Application No. 61/013,522 filed on Dec. 13, 2007 and U.S. Provisional Patent Application No. 61/021,781 filed on Jan. 17, 2008, both of these Provisional Patent Applications, the disclosures of which are expressly incorporated herein by reference.

STATEMENT OF GOVERNMENTAL RIGHTS

This invention was made with government support under R21 HL087816 awarded by National Institutes of Health. The government has certain rights in the invention.

TECHNICAL FIELD

Various aspects and embodiments relate generally to materials and methods for inhibiting the enzyme S-nitrosoglutathione reductase (GSNOR) and for diagnosing, studying and treating various conditions and diseases related to the activity of this enzyme.

BACKGROUND

S-nitrosylation of cellular proteins has emerged as the key reaction through which nitric oxide exerts its numerous effects inside the body. The growing list of proteins whose activities are regulated by s-nitrosylation include, ion channel proteins, kinases, proteolytic enzymes, transcription factors and proteins involved in energy transduction. In conjunction with s-nitrosylation of these proteins, nitric oxide has been shown to regulate processes and proteins involved in apoptosis, G-protein-coupled receptor based signaling, vascular tone, and inflammatory responses. Whereas s-nitrosylation of target proteins produces the effects of nitric oxide, the denitrosylation pathways terminate the effect of nitric oxide. The enzyme s-nitrosoglutathione reductase (GSNOR) is a member of the alcohol dehydrogenase family and has been shown to be the primary pathway through which cells denitrosylate intracellular proteins. GSNOR catalyzes the denitrosylation of intracellular proteins by the reduction of s-nitrosoglutathione (GSNO). Because of its role in the regulation of the s-nitrosylation of intracellular proteins, GSNOR has become an important target for developing agents that modulate nitric oxide bioactivity.

For example, nitric oxide and the s-nitrosylation de-nitrosylation cycle play an essential role in many pathologies. Various vascular disorders such as heart disease, heart failure, heart attack, hypertension, atherosclerosis, and restenosis are related to nitric oxide activity, and s-nitrosylation states. Similarly, conditions such as asthma and impotence are also linked to varying levels of nitric oxide bioactivity. Nitric oxide activity correlates with the level of GSNO metabolic intermediates in the cell. Nitric oxide activity and GSNO activity levels may also play a role in other disease including Parkinson's disease, Alzheimer's disease, amyotrophic lateral sclerosis, stroke, septic shock, cardiogenic shock, endotoxic shock, toxic shock syndrome, systemic inflammatory response syndrome, and other inflammatory diseases. The therapeutic potential of preventing the breakdown of s-nitrosothiols via inhibition of GSNOR has been demonstrated in a mouse model for asthma. Knockout mice lacking the genes for GSNOR were found to resist airway hyperresponsivity due to higher GSNO concentrations in bronchial fluids and diminished tachyphylaxis to β-agonists because of the s-nitrosylation of G-protein coupled receptor kinases.

Given its role in normal and abnormal cell physiology there is a need for compounds that modulate GSNOR activity and\/or method of using those compounds.

SUMMARY

One aspect of the invention is a compound and/or a method for altering enzyme activity, comprising the steps of: providing at least one compound selected from the group consisting of:

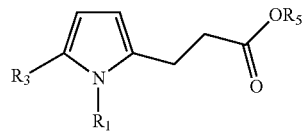

Wherein,

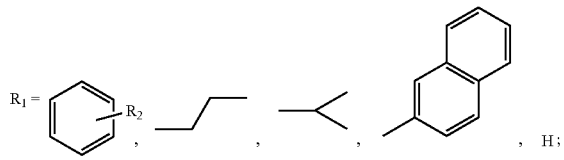

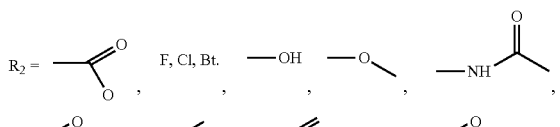

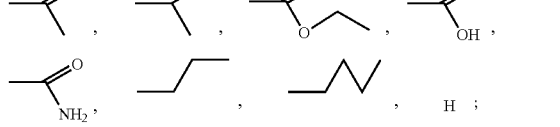

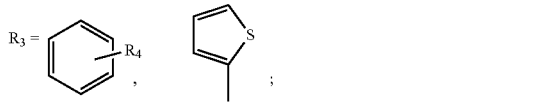

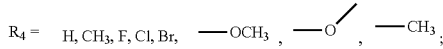

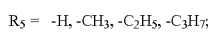

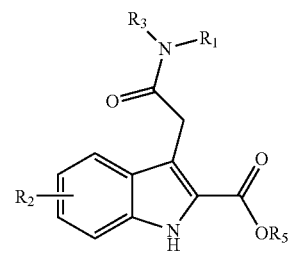

-continued $R_1$ = -$C_2H_5$, -H, -$CH_3$, -$C_3H_7$
$R_2$ = -H, -Cl, -F, -Br

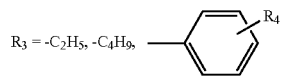

$R_4$ = -$OC_2H_5$, -$OCH_3$, -$C_2H_5$, -$C_2H_5$, -F, -Cl, -Br, -$OCH_3$, -$COOC_2H_5$
$R_5$ = =H, -$CH_3$, -$C_2H_5$, -$C_3H_7$;

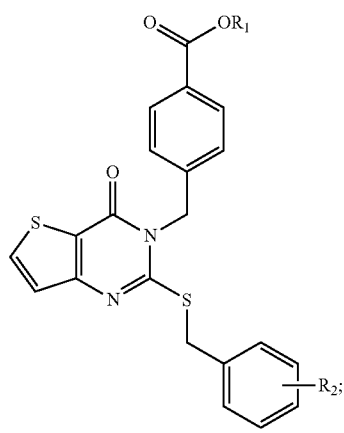

$R_1$ = ——H, ——$CH_3$, ——$C_2H_5$, ——$C_3H_7$
$R_2$ = ——H, ——CN, ——OH, ——$CH_2OH$ and

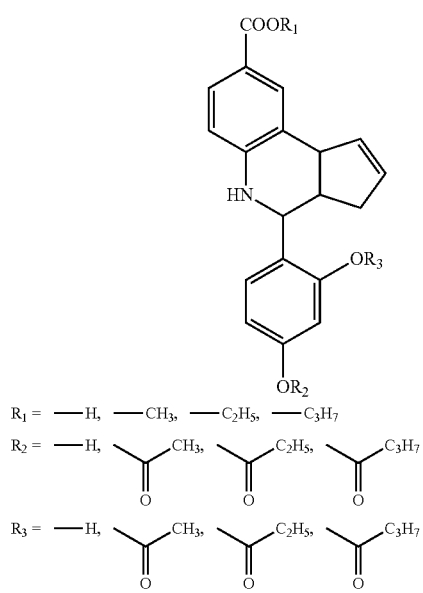

$R_1$ = ——H, ——$CH_3$, ——$C_2H_5$, ——$C_3H_7$
$R_2$ = ——H, $\overset{O}{\underset{}{\text{-C-}}}CH_3$, $\overset{O}{\underset{}{\text{-C-}}}C_2H_5$, $\overset{O}{\underset{}{\text{-C-}}}C_3H_7$
$R_3$ = ——H, $\overset{O}{\underset{}{\text{-C-}}}CH_3$, $\overset{O}{\underset{}{\text{-C-}}}C_2H_5$, $\overset{O}{\underset{}{\text{-C-}}}C_3H_7$ or a physiologically acceptable salt thereof; and contacting said compound with s-nitrosoglutathione reductase.

One embodiment is a method for treating a disease or a condition, comprising the steps of: providing at least one compound according to any of the compounds provided herein including those referred to in the above, and administering a therapeutically effective dose of said compound to a patient in need thereof. Still another embodiment is a method for treating a disease as outline in the above wherein the disease or condition is selected from the group consisting of: asthma, chronic obstructive pulmonary disease, heart disease, heart failure, heart attack, hypertension, atherosclerosis, restenosis, impotence, Parkinson's disease, Alzheimer's disease, amyotrophic lateral sclerosis, stroke, septic shock, cardiogenic shock, endotoxic shock, toxic shock syndrome, systemic inflammatory response syndrome, and other inflammatory diseases. In one embodiment the therapeutically effective amount of said compound in on the range of about 0.01 mg/kg per of body mass day to 1000 mg/kg of body mass per day.

Yet another embodiment is a method for diagnosing or studying a disease or a condition, comprising the steps of: providing at least one compound as disclosed in the above and contacting the compound with s-nitrosoglutathione reductase; an observing a change in conformity with a change in s-nitrosylation. In one embodiment the disease or condition being diagnosed is selected from the group consisting of: asthma, chronic obstructive pulmonary disease, heart disease, heart failure, heart attack, hypertension, atherosclerosis, restenosis, impotence, Parkinson's disease, Alzheimer's disease, amyotrophic lateral sclerosis, stroke, septic shock, cardiogenic shock, endotoxic shock, toxic shock syndrome, systemic inflammatory response syndrome, and other inflammatory diseases. Still another embodiment is a method of studying protein nitrosylation comprising the steps of: providing at least one compound according disclosed herein, including those name in the above and; contacting said compound with s-nitrosoglutathione reductase; and observing a change in s-nitrosylation. Another embodiment provides a kit for altering the activity of s-nitrosoglutathione reductase, comprising at least one compounds named in the above.

Still another embodiment includes provides a method for treating a disease or condition in which the disease or condition including the steps of providing at least one compound selected from the group consisting of:

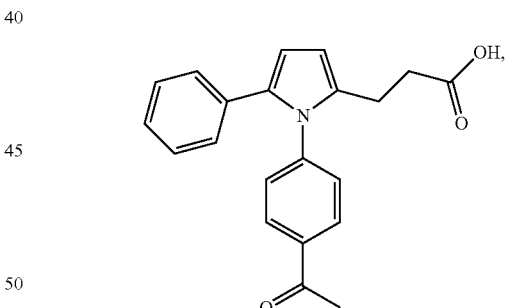

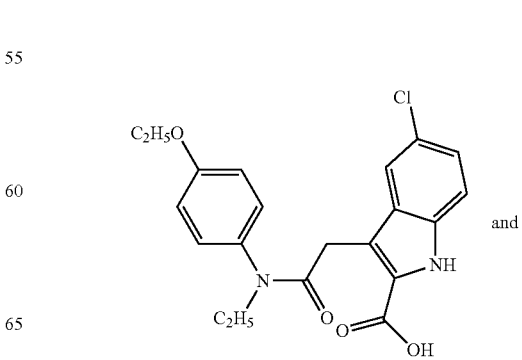

and

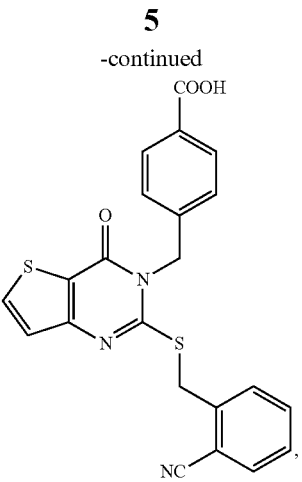

or a pharmaceutically acceptable salt or ester thereof; and administering a therapeutically effective dose of said compound to a patient in need thereof. In one embodiment the disease or condition is selected from the group consisting of: asthma, chronic obstructive pulmonary disease, heart disease, heart failure, heart attack, hypertension, atherosclerosis, restenosis, impotence, Parkinson's disease, Alzheimer's disease, amyotrophic lateral sclerosis, stroke, septic shock, cardiogenic shock, endotoxic shock, toxic shock syndrome, systemic inflammatory response syndrome, and other inflammatory diseases. In one embodiment the therapeutically effective amount of the compound used to treat a disease or condition in the range of about 0.01 mg/kg per of body mass day to 1000 mg/kg of body mass per day.

Still another embodiment provides a method for diagnosing or studying a disease, condition or chemical and/or enzymatic reaction including the steps of providing at least one compound selected from the group consisting of:

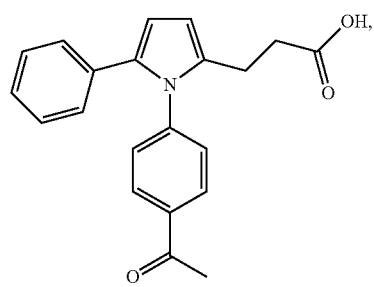

and

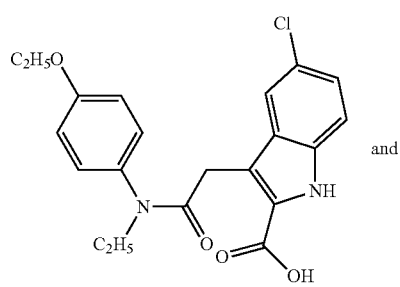

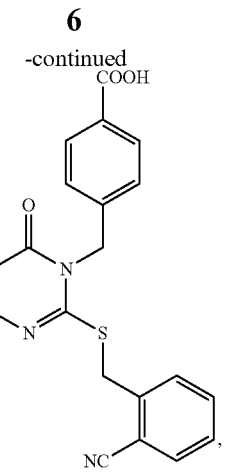

or a pharmaceutically acceptable salt or ester thereof; contacting said compound with s-nitrosoglutathione reductase; and observing a change in conformity with a change in s-nitrosylation. In one embodiment the disease and/or condition being diagnosed and/or studied is selected from the group consisting of: asthma, chronic obstructive pulmonary disease, heart disease, heart failure, heart attack, hypertension, atherosclerosis, restenosis, impotence, Parkinson's disease, Alzheimer's disease, amyotrophic lateral sclerosis, stroke, septic shock, cardiogenic shock, endotoxic shock, toxic shock syndrome, systemic inflammatory response syndrome, and other inflammatory diseases. Still another embodiment is kit for altering the activity of s-nitrosoglutathione reductase, comprising at least one of the compounds described in the above.

One aspect of the present invention provides compounds that can be used to inhibit the enzyme S-nitrosoglutathione reductase. These compounds include Compound A, Compound B, Compound C and Compound D, as well as all physiologically acceptable salts thereof.

One embodiment is a method of treating human or animals patients comprising the steps of providing at least one compound selected from the group comprising Compound A, Compound B, Compound C and Compound D or a physiological salt thereof and administering a therapeutically effective dose of the compound to a human or animal patient.

In still another embodiment is a method of diagnosing a disease in a human or an animal comprising the steps of providing at least one compound, selected from the group comprising Compound A, Compound B, Compound C and Compound D or a physiological salt thereof and contacting said compound with at least one enzyme in the human or animal.

Yet another embodiment is a method of studying the mechanism, chemistry or role in physiology of the enzyme s-nitrosoglutathione reductase either in vitro or in vivo comprising the steps of providing at least one compound selected from the group comprising Compound A, Compound B, Compound C and Compound D or a physiological salt thereof and contacting said compound with the enzyme s-nitrosoglutathione reductase.

One embodiment is a method of treating, diagnosing, curing, controlling or other wise affecting a disease, defect or other medical condition treated by administering a therapeutically effective dose of at least one of the following compounds selected from the group including Compound A, Compound B, Compound C and Compound D or a physiological salt thereof. In one embodiment the condition affected is selected from the group comprising the activation of elements of the immune system including, but not limited to, macrophages, thymocytes, lymphocytes, or intercellular networks that involve nitric oxide signaling networks, cellular processes such as apoptosis, the activity of endothelial cells, vascular disorders such as heart attack, heart disease, heart failure, hypertension, restenosis, impotence, atherosclerosis and the like In another embodiment of the invention the condition affected is selected from diseases of the lung including asthma, chronic obstructive pulmonary disease, and cystic fibrosis.

BRIEF DESCRIPTION OF THE FIGURES

FIG. 7 represents a table illustrating structures of some inhibitors of GSNOR.

FIG. 8 represents data illustrating inhibition of various alcohol dehydrogenase isozymes by compounds that inhibit the enzyme GSNOR.

FIG. 9 represents a summary of kinetic data consistent with mechanism of GSNOR inhibition by various compounds.

FIG. 10B represents kinetic data measured with various exemplary compounds thought to inhibit GSNOR.

FIG. 10C represents kinetic data measured with various exemplary compounds thought to inhibit GSNOR.

FIG. 10D represents kinetic data measured with various exemplary compounds thought to inhibit GSNOR.

FIG. 10H represents kinetic data measured with various exemplary compounds thought to inhibit GSNOR.

FIG. 10I represents kinetic data measured with various exemplary compounds thought to inhibit GSNOR.

DETAILED DESCRIPTION

Figure 1:
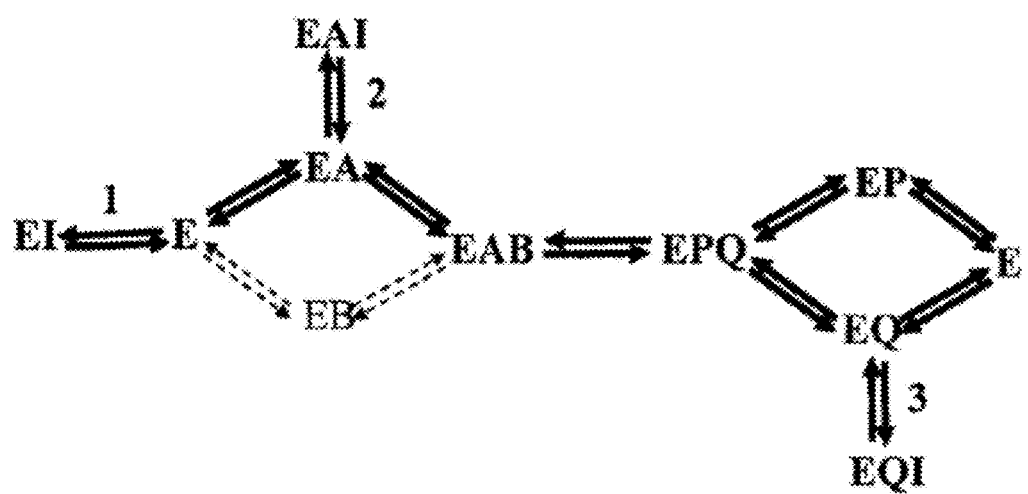
FIG. 1 is a diagram illustrating the Kinetic mechanism of GSNOR and the types of complexes that an inhibitor binding to the GSNO site could form along the kinetic pathway of GSNOR.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

The enzyme S-nitrosoglutathione reductase (GSNOR) catalyzes the removal of nitro groups from nitrosylated proteins. GSNOR is generally categorized as a member of the alcohol dehydrogenase family of enzymes; its physiological substrates are thought to be nitrosylated proteins, S-nitrosoglutathione (GSNO) and NADH. Nitrosylated intercellular proteins are often the result of nitric oxide bioactivity and these proteins account for much of nitric oxide's physiological effects. Accordingly, the denitrosylation reaction catalyzed by GSNOR helps healthy, normal cells to maintain a balance between nitrosylated and de-nitrosylated proteins and functions as an integral part of the cycle that modulates the effects of nitric oxide and its attendant effects.

We have identified a number of compounds including substituted pyrroles, indoles, thiophenes and aromatic rings that affect the activity of GSNOR and therefore may be used to modulate the effect nitric oxide's effect on intercellular proteins and on physiology. One aspect includes molecules having the structure generally referred to as Compound A and using the same to treat and/or diagnose various diseases and/or conditions or to study various enzyme catalyzed reactions; these molecules have the following generic structure and include pharmaceutically acceptable salts and/or esters thereof:

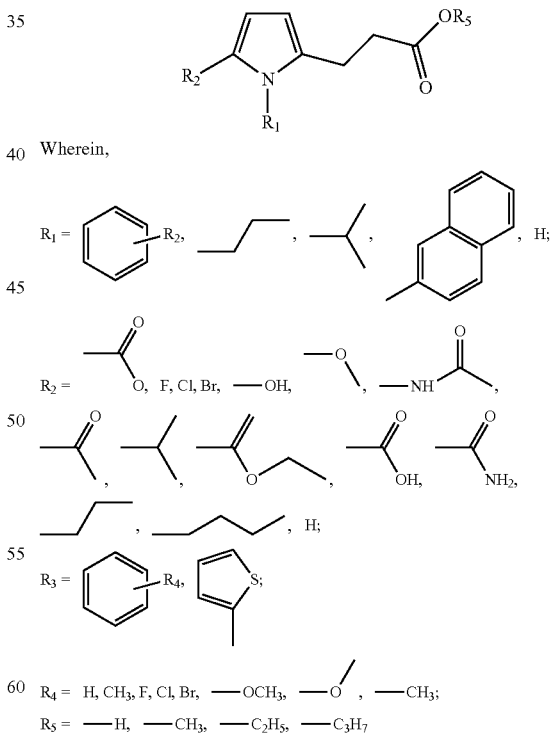

Another aspect includes molecules having the structure generally referred to as Compound B and using the same to treat and/or diagnose various diseases and/or conditions or to study various enzyme catalyzed reactions; these molecules have the following generic structure and include pharmaceutically acceptable salts and/or esters thereof:

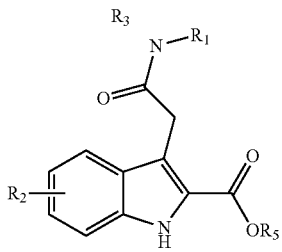

R$_1$ = —C$_2$H$_5$, —H, —CH$_3$, —C$_3$H$_7$
R$_2$ = —H, —Cl, —F, —Br
R$_3$ = —C$_2$H$_5$, —C$_4$H$_9$, ⌬—R$_4$
R$_4$ = —OC$_2$H$_5$, —OCH$_3$, —C$_2$H$_5$, —F, —Cl, —Br, —OCH$_3$, —COOC$_2$H$_5$
R$_5$ = —H, —CH$_3$, —C$_2$H$_5$, —C$_3$H$_7$

Still another aspect includes molecules having the structure generally referred to as Compound C and using the same to treat and/or diagnose various diseases and/or conditions or to study various enzyme catalyzed reactions; these molecules have the following generic structure and include pharmaceutically acceptable salts and/or esters thereof:

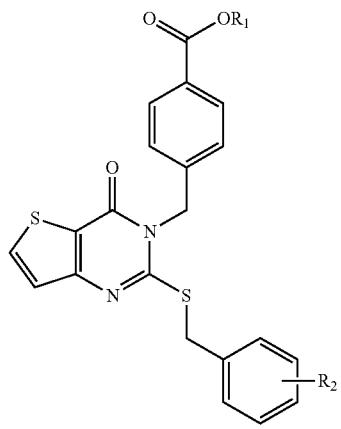

R$_1$ = —H, —CH$_3$, —C$_2$H$_5$, —C$_3$H$_7$
R$_2$ = —H, —CN, —OH, —CH$_2$OH

Yet another aspect includes molecules having the structure generally referred to as Compound D and using the same to treat and/or diagnose various diseases and/or conditions or to study various enzyme catalyzed reactions; these molecules have the following generic structure and include pharmaceutically acceptable salts and/or esters thereof

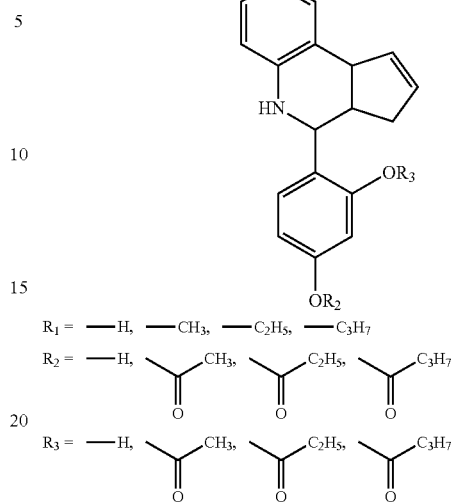

R$_1$ = —H, —CH$_3$, —C$_2$H$_5$, —C$_3$H$_7$
R$_2$ = —H, ⟶C(=O)CH$_3$, ⟶C(=O)C$_2$H$_5$, ⟶C(=O)C$_3$H$_7$
R$_3$ = —H, ⟶C(=O)CH$_3$, ⟶C(=O)C$_2$H$_5$, ⟶C(=O)C$_3$H$_7$

Synthesis of the backbone is given in Synthesis 1. Additional synthesis detected can be found in the publication, *Journal of Medicinal Chemistry*, 1997, vol. 40, No. 11.

The compounds useful in the invention may be delivered not only as single agents by the oral, inhalation or parenteral route but also in the form of cocktails which are mixtures of other appropriate compounds to treat a particular disease. The use of cocktails in the treatment of asthma, cardiovascular disease and other diseases treated by the invention is routine. In this embodiment, a common administration vehicle (e.g., pill, tablet, implant, injectable solution, etc.) would contain both the compound useful in this invention and the additional therapeutic drug and/or supplementary potentiating agent.

The compounds of the invention when used alone or in cocktails are administered in therapeutically effective amounts. A therapeutically effective amount will be determined by the parameters discussed below; but it is that amount which establishes a level of the drug(s) in the area of the blood stream or tissue to be treated, such as the lung or vascular smooth muscle, which is effective in causing a therapeutic benefit.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts. Furthermore, included along with the compounds of Groups A, B, C, and D are their pharmaceutically acceptable salts, including base addition salts. The term pharmaceutically-acceptable salts include salts commonly used to form alkali metal salts and to form addition salts of free bases. The nature of the salt is not critical, provided that it is pharmaceutically acceptable.

Suitable pharmaceutically-acceptable base addition salts of the compounds of the invention may be prepared from an inorganic base or an organic base. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, and procaine. All of these salts may be prepared by conventional means from the corresponding compounds of the invention by reacting, for example, the appropriate base with one of the compounds of the invention.

Also included in the invention are the pharmaceutically acceptable esters of compounds of the invention. These esters may be prepared by an acid catalyzed reaction between the compounds of the invention and an alcohol like methanol, ethanol, isopropyl, butanol and other alkyl and aryl alcohols.

Suitable buffering agents include, for example, acetic acid and a salt (1-2% W/V); citric acid and a salt (1-3% W/V); boric acid and a salt (0.5-2.5% W/V); and phosphoric acid and a salt (0.8-2% W/V).

Suitable preservatives include benzalkonium chloride (0.003-0.03% W/V); chlorobutanol (0.3-0.9% W/V); parabens (0.01-0.25% W/V) and thimerosal (0.004-0.02% W/V).

The invention is also directed to pharmaceutical compositions and/or formulations comprising, for example, at least one of the following Compound 6, 7 or 8 (Table 1) or the like and pharmaceutically acceptable salts and/or esters thereof and at least one pharmaceutically acceptable carrier or diluent, as well as methods for using the same to treat and or diagnose various diseases of conditions a well as methods for studying various chemical and biological processes.

The formulations of the present invention can be solutions, suspensions, syrups, tablets, capsules, and the like. The compositions may contain a suitable carrier, diluent, or excipient, such as a medium chain triglyceride oil or magnesium stearate. In preferred formulations, a medium chain triglyceride oil and magnesium stearate is present in an approximately 1:1 ratio. Standard texts, such as Remington's Pharmaceutical Science, 18th Ed., 1990, incorporated herein by reference, may be consulted to prepare suitable preparations, without undue experimentation.

One preferred carrier is polyethylene glycol (PEG). One more preferred is a mixture of polyethylene glycol having a high molecular weight, for example of greater than 900 (most preferably, about 1,000), and polyethylene glycol having a low molecular weight, for example of less than 500 preferably about 400).

One particularly preferred carrier is PEG in the ratio of about one part PEG with a MW of 100 to about two parts PEG with a MW of about 400.

Preferred emulsifiers include phosphatidylcholine emulsifiers, such as dilauroylphosphatidylcholine.

The formulations can include powdered carriers, such as lactose, sucrose, mannitol, starch, cellulose derivatives, xanthum gum, magnesium stearate, stearic acid, and the like.

The composition may also comprise a penetration enhancer. Suitable penetration enhancers include glycerol, glycerol monolaureate, dimethyl sulfoxide or oils, such as a mineral oil or medium chain triglyceride oil.

Antioxidants such as, for example butylated hydroxytoluene (BHT), sodium bisulfate, sodium sulfite, sodium EDTA, ascorbic acid, and the like can be used either alone or in combination with other suitable antioxidants or stabilizing agents typically employed in pharmaceutical compositions.

The formulations can also include any of the commonly used disintegrants, lubricants, plasticizers, colorants, and dosing vehicles. Suitable pharmaceutical carriers are described in Remington's Pharmaceutical Sciences, a standard reference text in this field. Suitable formulations typically contain from about 1 to about 1000 mg of active ingredient per dosage unit. In these pharmaceutical compositions, the active ingredient will ordinarily be present in an amount of about 0.5 to about 95%, by weight, based on the total weight of the composition.

The magnitude of the therapeutic dose of the compounds of the invention will vary with the nature and severity of the condition to be treated and with the particular route of administration.

Although the most suitable route in any given case will depend largely on the nature and severity of the condition being treated and on the nature of the active ingredient, the compositions of the invention may be conveniently presented in unit dosage form and prepared by any of the methods well known in the art of pharmacy.

The active compounds of the present invention may be a pharmaceutical composition having a therapeutically effective amount of a conjugate of the invention optionally included in a pharmaceutically-acceptable carrier. The term "pharmaceutically-acceptable carrier" as used herein means one or more compatible solid or liquid fillers, diluents, or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy.

Compositions suitable for parenteral administration conveniently comprise a sterile preparation of the compounds of the invention. This preparation may be formulated according to known methods. The sterile preparation thus may be a sterile solution or suspension in a non-toxic parenterally-acceptable diluent or solvent. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

A subject or patient, as used herein means humans, primates, horses, cows, pigs, sheep, goats, dogs, cats and rodents.

The compounds of the invention are administered in effective amounts. An effective amount is an amount necessary to delay the onset of, inhibit the progression of, halt altogether the onset of, or progression of, to diagnose the particular condition being treated. For example, in general, an effective amount for treating asthma will be that amount necessary to open airways and decrease airway inflammation such that a therapeutic benefit results. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosage may be adjusted appropriately to achieve desired drug levels, locally or systemically. Generally, daily oral doses of active compounds will be from about 0.01 mg/kg per day to 1000 mg/kg per day. It is expected that IV doses in the range of about 1 to 1000 mg/m$^2$ per day will be effective. In the event that the response in a subject is insufficient at such doses, even higher doses (or effective higher doses by a different, more localized delivery route) may be employed to the extent that patient tolerance permits. Continuous IV dosing over, for example 24 hours or multiple doses per day are also contemplated as necessary to achieve appropriate systemic levels of the compounds. Likely, preferred dosing schedules, including concentration, length of administration, and the like are described herein.

A variety of administration routes are available. The particular mode selected will depend of course, upon the particular drug selected, the severity of the disease state being treated and the dosage required for therapeutic efficacy. The methods of this invention, generally speaking, maybe practiced using any mode of administration that is medically acceptable, meaning any mode that produces effective levels of the active compounds without causing clinically unacceptable adverse effects. Such modes of administration include, for example, oral, rectal, sublingual, topical, nasal, transdermal, intradermal or parenteral routes. The term "parenteral" includes subcutaneous, intravenous, intramuscular, or infusion. In some instances intravenous routes may be preferred.

The compositions may conveniently be presented in unit dosage form and may be prepared by any of the methods well known in the art of pharmacy. All methods include the step of bringing the conjugates of the invention into association with a carrier which may constitute one or more accessory ingredients. In general, the compositions may be prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions may include, for example, suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, may mean that the implant is constructed and arranged to deliver therapeutic levels of the active ingredient for at least 30 days, and in some instances 60 days or longer. Long-term sustained release implants are well known to those of ordinary skill in the art and include some of the release systems described above. Such implants can be particularly useful in treating chronic conditions such as asthma and cardiovascular diseases.

The compounds of the invention are also useful, in general, for treating disease and conditions including, but not limited to asthma, chronic obstructive pulmonary disease, heart disease, heart failure, heart attack, hypertension, atherosclerosis, restenosis, impotence, Parkinson's disease, Alzheimer's disease, amyotrophic lateral sclerosis, stroke, septic shock, cardiogenic shock, endotoxic shock, toxic shock syndrome, systemic inflammatory response syndrome, and other inflammatory diseases. Those skilled in the art will be able to recognize with no more than routine experimentation numerous equivalents to the specific products and processes described above. Such equivalents are intended to be included within the scope of the appended claims.

All references disclosed herein are incorporated by reference.

Results and Discussion

Identification of Compounds that Inhibit GSNOR at Physiological pH:

GSNOR is an alcohol dehydrogenases and like other members of ADH family, is capable of oxidizing and reducing primary alcohols and aldehydes with the help of a molecule of NAD(H). Octanol was chosen as the substrate in the initial screening assay as it is bulky like GSNO, but has 200-fold higher $K_M$ value (1 mM) and a $k_{cat}$ value (200 min-1) that is more than 2 order of magnitude lower than that of GSNO. This allows the initial velocity conditions to prevail for a period up to 10 min (data not shown) and it enables conducting a large number of concurrent assays in a 384 well plate format. The pH of the assay was adjusted to pH 10 in order to get significant rate of oxidation of octanol in the absence of compounds. The screening for GSNOR inhibitors was performed in the presence of saturating concentration of NAD$^+$ and an un-saturating concentration of octanol thereby increase the probability of identifying compounds that bind, only or primarily in the GSNO binding site of GSNOR. This was deemed desirable as there are many dehydrogenases inside the cells and compounds binding in the coenzyme binding site are more likely to be nonspecific inhibitors of GSNOR, than compounds that bind primarily to the form of GSNOR that binds GSNO.

Compounds that inhibited the rate of octanol oxidation by 40% or more in the initial screening assay were selected for further analysis. The GSNOR inhibitory activity of the initially identified compounds was confirmed at pH's 10 and 7.5 using 12-hydroxydodecanoic acid and s-nitrosoglutathione as substrates, respectively. Table 1 lists representative compound from each of the eight different classes of compounds identified in the initial screening experiment. Each of the identified compounds in Table 1 was a better inhibitor of GSNOR than the existing GSNOR inhibitor, dodecanoic acid, at inhibiting GSNOR at pH 10. Still referring to Table 1, compound 6-8 inhibited GSNOR more effectively at pH 10 (53-97% inhibition) than at pH 7.5 (1.7-35% inhibition). The decrease in the affinity of these compounds at pH 7.5 is likely to be due to the change in the ionization status of their ionizable groups at lower pH. Both the imidamide group in compound 1 and the pyridinyl nitrogen in compound 2 would be more protonated at pH 7.5 than at pH 10 and be repelled by a similarly charged residue in the GSNOR active site. Compound 8 also displays higher GSNOR inhibition at pH 10 than at pH 7.5. However it has a phenolic hydroxyl group whose ionization state would be suppressed significantly at pH 7.5. It is possible that the ionized phenolic hydroxyl group is involved in an important interaction with an oppositely charged residue within the GSNOR active site. It is likely that compounds 6-8 could serve as effective GSNOR inhibitors at physiological pH only if the charge on their ionizable group is reversed or their $pK_a$ values perturbed significantly; accordingly, compounds 6-8 were not characterized further.

Compounds 4-8 appear to be especially promising inhibitors of GSNOR as they appeared to maintain their affinity for the GSNOR active site at both of the pHs we assayed. These compounds also exhibited hundred fold lower $IC_{50}$ values than does dodecanoic acid measured at physiological pH. Referring now to compound 5, the removal of the ester group significantly improved the affinity of the inhibitor for GSNOR as evidenced by a three fold higher inhibition of GSNOR by the hydrolyzed form of the compound (Table 1). Compounds 4-8, meet Lipinski's five point rule for small molecules with drug-like properties and appeared to be good candidates for further investigation as inhibitors of GSNOR.
Selectivity of GSNOR Inhibition:

The ability of compounds 4-8 to selectively inhibit GSNOR as opposed to some other alcohol dehydrogenases (ADHs) was determined this was deemed to be important as most ADHs have a similar overall structure, and broad substrate specificity Inhibition of three additional isozymes of ADH family specifically, $\beta_2\beta_2$-, $\pi$-, and $\sigma$-ADHs by the same concentration of compounds 4-8 was examined along with that of GSNOR. In each case, the inhibition assay was conducted in the presence of saturating or $K_M$ concentrations of the coenzyme and the alcohol substrate. Referring now to Table 2, compounds 6-8 are highly specific inhibitors of GSNOR. At concentrations that inhibit more than 70% of GSNOR activity, there is no significant inhibition of any of the other ADH isozymes tested with compounds 6-8. Compound 4 inhibited $\pi$-ADH more than GSNOR and it was not studied any further. Compounds 5, while being a modestly good inhibitor of GSNOR, also showed significant inhibition of $\sigma$-ADH. Accordingly, further modifications of compound 5 may be necessary to improve its selectivity for GSNOR over the other ADH isozymes. Compounds 6-8 show promise as highly effective and selective inhibitors of GSNOR and were selected as lead compounds for further investigation.
Determining the Mechanism of Inhibition of GSNOR by Compounds 6-8:

Dead-end inhibition and fluorescence studies were performed to identify the binding site of compounds 6-8 as they appeared to have very little similarity with any of the known GSNOR substrates or inhibitors. Referring now to Table 3, the inhibitors tested exhibited noncompetitive and uncompetitive inhibition against varied concentrations of either GSNO or NADH. This may indicate that neither of these substrates can completely prevent compounds 6-8 from binding to GSNOR. This would occur if, for example, compounds 6-8 were binding to multiple enzyme complexes occurring in the kinetic pathway (shown in FIG. 1). Inhibition by binding to a site outside the active site in GSNOR is unlikely since the type of inhibition by the compounds against NADH and GSNOR would have been similar. An additional dead-end inhibition study involving dodecanoic acid as inhibitor against varied GSNO was performed to determine the type of complexes that an inhibitor binding in the substrate binding site would form in the kinetic pathway of GSNO reduction.

Referring now to FIG. 1, GSNOR may have a preferred kinetic pathway (shown by the bold lines) through GSNOR•NADH complex (EA) in its random mechanism during the reduction of aldehyde. In this proposed mechanism the aldehyde (B), can bind to the free form of GSNOR (E), or preferentially to the GSNOR•NADH complex (EA) to form the competent ternary complex (EAB). The EAB complex undergoes catalysis to form the products, $NAD^+$ (Q) and alcohol (P). After catalysis, either of the products can leave the enzyme. A GSNO inhibitor can bind to the free form of GSNOR (step 1), GSNOR•NADH (step 2) and GSNOR•$NAD^+$ (step 3) binary complexes to form EI, EAI and EQI ternary complexes, respectively.

Referring to Table 3, dodecanoic acid was found to be a noncompetitive inhibitor against varied GSNO concentration, even though it binds at the GSNO binding site. The noncompetitive inhibition of GSNOR by dodecanoic acid can be explained on the basis of the kinetic mechanism of GSNOR (shown in FIG. 1), during the reduction of aldehyde, 12-oxododecanoic acid (12-ODDA). GSNOR has a preferred kinetic pathway through the E•NADH complex during the reduction of 12-ODDA. Consistent with this mechanism dodecanoic acid would act as a noncompetitive inhibitor against varied GSNO levels if it binds to GSNOR at more than one place in the kinetic pathway; e.g., one where it competes with GSNO to bind to the enzyme (steps 1 and 2 in scheme 1) and one where GSNO does not normally bind in the kinetic pathway (step 3 in scheme 1). Competition with GSNO for binding to GSNOR would involve binding the inhibitor to the E•NADH complex (step 1) and to a small extent, to the free enzyme (step 2) and give rise to the slope effect closured in the double reciprocal plot of the kinetic data. Binding to GSNOR in the kinetic pathway where GSNO does not normally bind would involve binding the inhibitor to E•$NAD^+$ complex and will give rise to the intercept effect in the double reciprocal plot. The noncompetitive inhibition of GSNOR by compounds 6-8 against varied concentrations of GSNO can also be explained by their forming complexes with E•NADH•I and E•$NAD^+$•I. The uncompetitive inhibition by compounds 6 and 8 and almost uncompetitive inhibition by compound 7 (although inhibition by compound 7 statistically fits noncompetitive mechanism better, the $K_{is}$ value is five fold higher than the $K_{ii}$ value and has high standard errors) against varied NADH can be explained by the compounds binding to the E•NADH complex in the nearly ordered kinetic mechanism of GSNOR during aldehyde reduction and the high affinity of NADH ($K_D$=0.05 μM) for GSNOR. Both these factors would make the contribution of E•I very small in the inhibition of the enzyme under the experimental conditions and make the inhibition uncompetitive. The inhibition of GSNOR caused by binding compounds 6-8 to the enzyme at more than one place in the kinetic pathway is similar to that shown by Sulfoxide and amide inhibitors of horse liver alcohol dehydrogenase.

Equilibrium binding studies were conducted to test the hypothesis formulated to account for the dead-end inhibition studies, namely that compounds 6-8 (Table I) were binding in the substrate (GSNO or any alcohol and aldehyde) binding site. If compounds 6-8 were to bind in the substrate binding site, they should exclude only the substrate and not the coenzyme from the GSNOR active site.

Figure 2A:
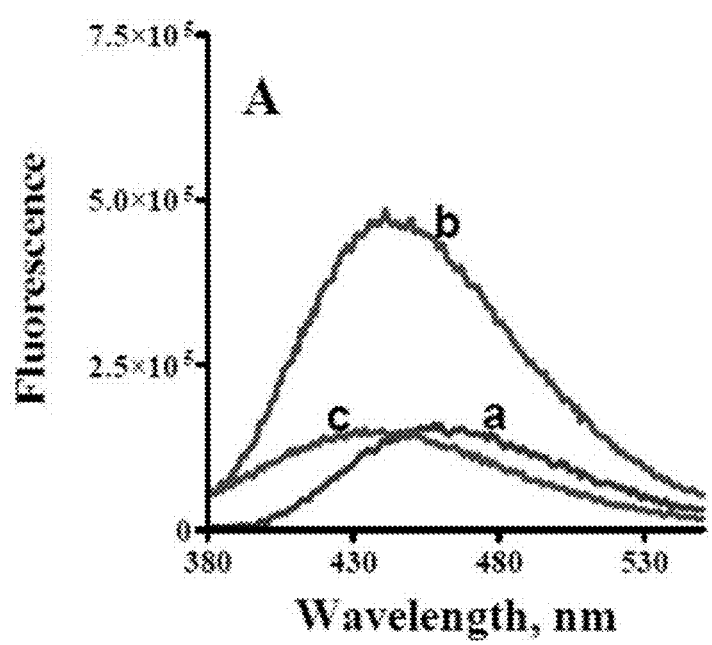
FIG. 2A illustrates the changes in the fluorescence of NADH (curve a) upon sequential addition of GSNOR (curve b) and compound 8 (curve c).
Figure 2B:
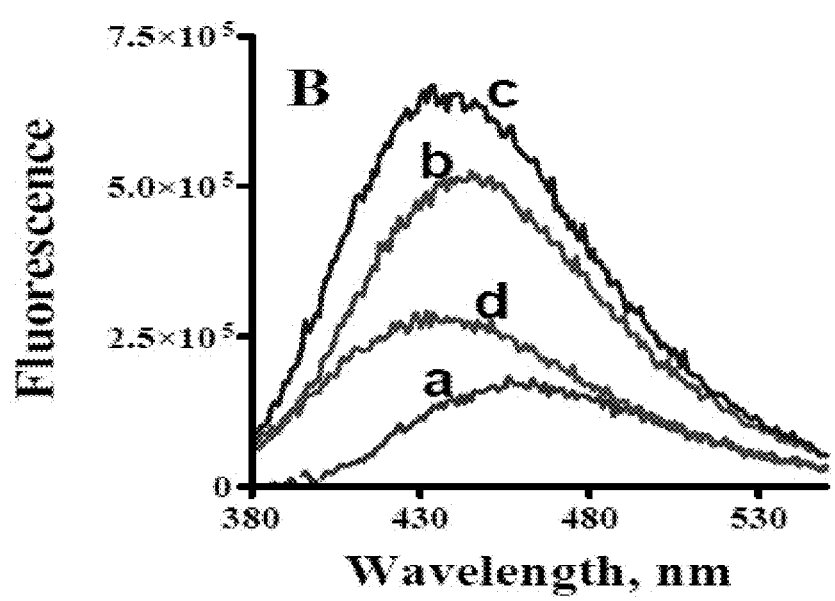
FIG. 2B illustrates the changes in the fluorescence of NADH (curve a) upon sequential addition of GSNOR (curve b), 12-HDDA (curve c) and compound 8 (curve d).
Figure 2C:
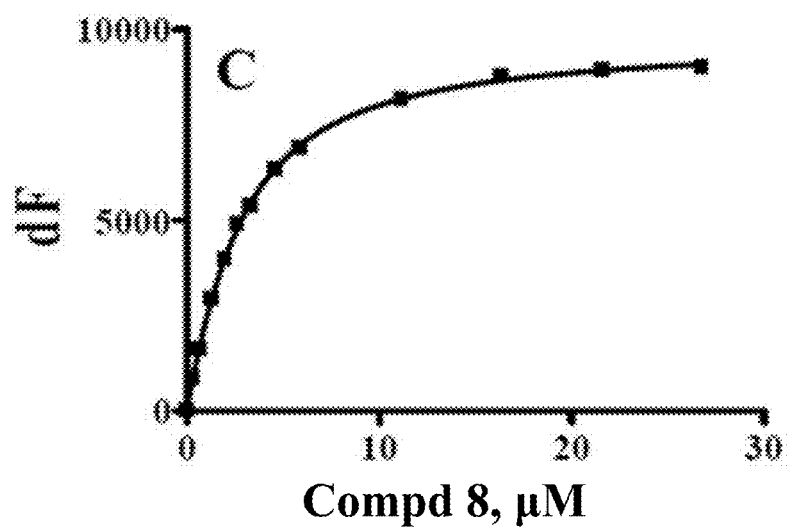
FIG. 2C illustrates the binding of compound 8 to GSNOR•NADH complex.

Referring now to FIG. 2, (A) Changes in the fluorescence of NADH (curve a) upon sequential addition of GSNOR (curve b) and compound 8 (curve c). To a solution of 1.7 μM NADH were added 2 μM GSNOR and 50 μM compound 8 in sequence and the fluorescence of the solution measured each time ($\lambda_{exc}$=350 nm; $\lambda_{emm}$=375-550 nm); (B) Changes in the fluorescence of NADH (curve a) upon sequential addition of GSNOR (curve b), 12-HDDA (curve c) and compound 8 (curve d). To a solution of 1.7 μM NADH were added 2 μM GSNOR, 810 μM 12-HDDA and 50 μM compound 8 in sequence and the fluorescence measured each time ($\lambda_{exc}$=350 nm; $\lambda_{emm}$=375-550 nm); (C) Binding of compound 8 to GSNOR•NADH complex. The change in fluorescence of a 1.7 µM NADH and 2 µM GSNOR mixture ($\lambda_{exc}$=350 nm; $\lambda_{emm}$=455 nm) with increasing concentrations of compound 8 was fitted to a single site binding model (equation 1; see materials and methods) using the Graphpad Prizm 4. All of the fluorescence studies were conducted at room temperature in 50 mM potassium phosphate pH 7.5.

Still referring to FIG. 2a, the fluorescence of NADH increases and shifts to a lower wavelength as NADH transfers from the polar environment in the solvent to the less polar environment within the GSNOR active site. The addition of compound 8 decreased the fluorescence of NADH but interestingly, there is a blue shift in the emission peak indicating that NADH is still in the nonpolar environment of the active site (compare curve a and c in FIG. 2a). Such a quenching of the fluorescence of the dihydropyridine ring has been observed when the amide inhibitors bind to Horse liver ADH•NADH complex. Compounds 6 and 7 also quenched the NADH fluorescence while moving the emission maxima to a shorter wavelength (data not shown). This suggests that compounds 6-8 do not exclude NADH from its binding site and are forming an E•NADH•Inhibitor complex.

In order to determine the effect of compounds 6-8 on the binding of the substrate, binding studies were conducted in the presence of the alcohol substrate, 12-hydroxydodecanoic acid (12-HDDA). The formation of GSNOR•NADH•12-HDDA abortive ternary complex has been reported earlier. Referring to FIG. 2b curve c 12-HDDA binds to GSNOR•NADH complex with a dissociation constant of 170 µM and increases the fluorescence of NADH in the ternary complex as shown in the figure. The addition of the same amount of compound 8 as used in the assay reported in FIG. 2a quenches the NADH fluorescence and results in a spectrum (FIG. 2b curve d). Shown in FIG. 2b curve d, it is similar to results described with E•NADH•Compound 8 complex formation suggesting that compound 8 has displaced 12-HDDA from the active site to form GSNOR•NADH•Compound 8 complex (i.e., curve c has higher fluorescence than that observed in FIG. 2a curve c because not all of the 12-HDDA bound to the enzyme has been displaced by compound 8). Compounds 6 and 7 also exhibit a similar effect on the fluorescence of GSNOR•NADH•12-HDDA complex. These binding experiments demonstrate that compounds 6-8 exclude only the alcohol/aldehyde substrate from binding into the active site.

Referring now to FIG. 2a the fluorescence change observed upon the formation of the GSNOR•NADH•Inhibitor complex was used to determine the equilibrium dissociation constant of the inhibitors for the GSNOR•NADH complex. The equilibrium dissociation constant of compounds 6-8 is less than 10 µM indicating that these compounds have high affinity for the GSNOR•NADH complex. Compounds 6 and 8 have significantly higher affinity for the GSNOR•NADH complex than compound 7 as evidenced by their 3-5 fold lower equilibrium dissociation constant.

Inhibition of GSNOR Inside the Cells

Figure 3A:
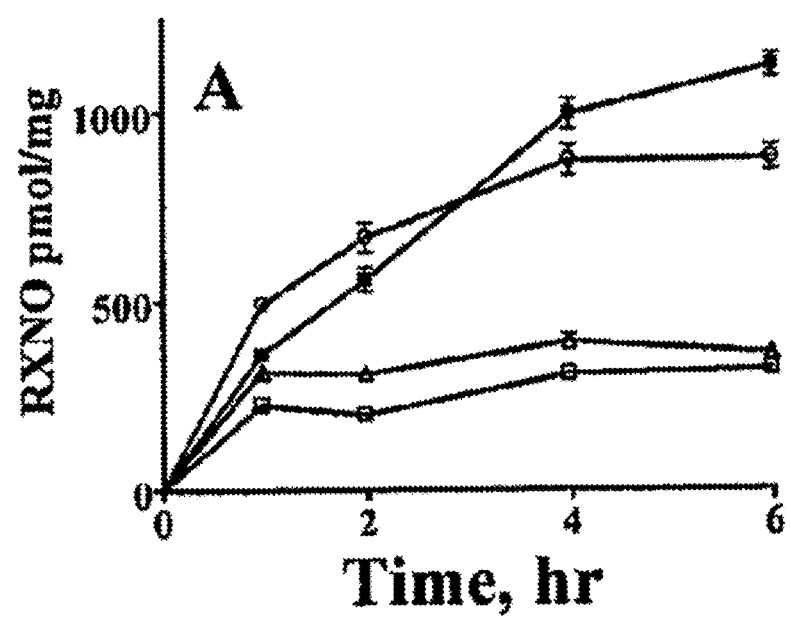
FIG. 3A illustrates data consistent with an increase in the accumulation of nitroso species in RAW 264.7 cells in presence of GSNOR inhibitors.

The ability of compounds 6-8 (Table I) to inhibit GSNOR inside the cells was tested in rat macrophages (RAW 264.7 cells). RAW cells have been used extensively as a model system for examining nitric oxide and s-nitrosothiol biochemistry. Briefly, RAW cells were treated with the inhibitors alone or in combination with GSNO and the intracellular nitrosylated species were quantitated using the triiodide based chemiluminescence method. Referring now to FIG. 3A no significant amounts of nitroso species were detected in untreated cells and cells exposed only to the compounds at concentrations used in these assays. A significant buildup of nitrosylated compounds was evident in cells treated with 500 µM GSNO. The nitrosylated compounds appeared to reach an equilibrium level within 1 hour of exposure to GSNO and remained fairly constant for the duration of 6 hours. In contrast, nitrosylated compounds continued to accumulate in cells treated with GSNO and 33 µM concentrations of either compound 6 or 8. At 6 hours the levels of nitrosylated species inside the cells treated with GSNO and compounds 6 or 8 were 3 to 4 fold higher than the level of nitrosylated species found in cells treated with GSNO alone. Still longer exposure of cells to compounds 6 or 8 (for up to 24 hours) resulted in an 80% decrease in the amounts of nitrosylated species measured at 4 hours (data not shown). (These results are consistent with temporary inhibition of the GSNOR rather than permanent inhibition of the enzyme.) Compound 7 (Table I) was not as effective as compounds 6 or 8 in inhibiting GSNOR inside the cells. This is evidenced by only a 1.3-1.7 fold increase in the levels of nitrosylated species and the shorter duration of its effect as judged from an insignificant difference in the levels of nitrosylated species measured at 6 hrs. An analysis of the molecular size of the nitrosylated species inside the treated cells showed that more than 95% of the nitrosylated species were greater than 5 kDa in size. Furthermore, 21-28% of the nitrosylated species in treated cells were resistant to mercury pretreatment, suggesting that N-nitrosothiolated proteins were also getting formed inside the cells. These observations indicate that compound 6-8 are inhibiting GSNOR inside the cells. It is also evident that GSNOR regulates the degree of nitrosylation of intracellular proteins by exogenously derived nitrosylating species.

The effect of varied concentrations of compounds on the accumulation of nitrosylated compounds was examined to compare the effectiveness of compounds 6-8 in inhibiting intracellular GSNOR. The level of intracellular nitrosylation increased with increasing concentration of the compounds in the medium. Compounds 6 and 8 are more effective at inhibiting GSNOR inside the cells than is Compound 7 as evident from the 3 fold higher nitrosylation observed at the 33 µM initial concentration. Although Compound 7 is less effective at inhibiting GSNOR inside the cells the either compound 6 or 8, it is nevertheless capable of raising the levels of nitroso compounds to the same extent as the other compounds.

Figure 4:
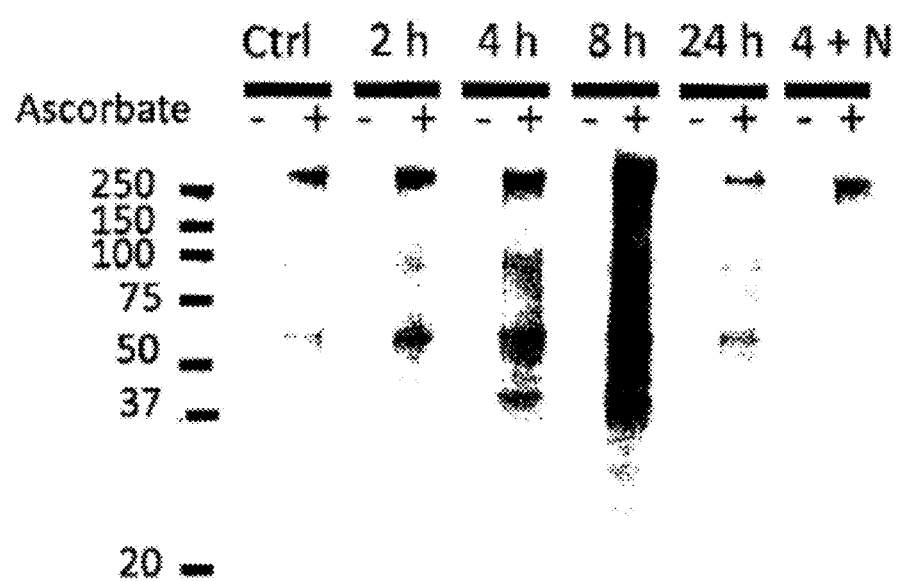
FIG. 4 illustrates the effects of Compound 8 on the nitrosylation of cellular proteins.
Figure 6:
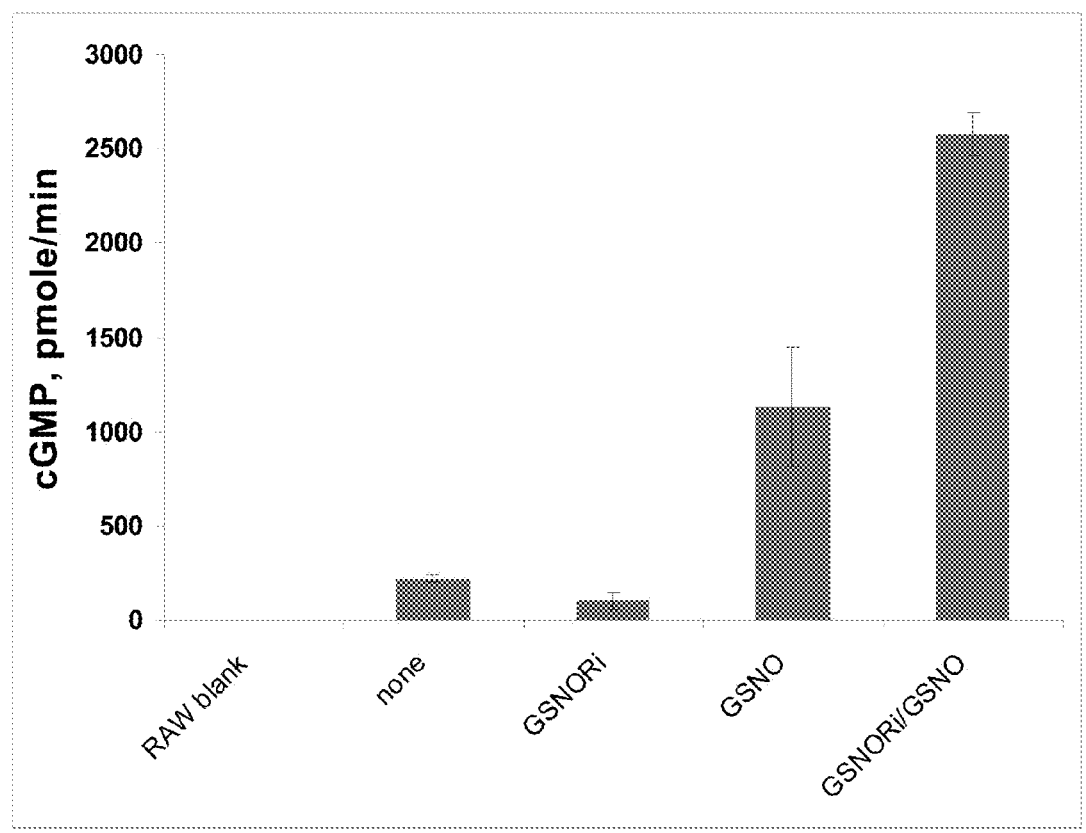
FIG. 6 illustrates that inhibition of GSNOR increases cGMP production.
Figure 10A:
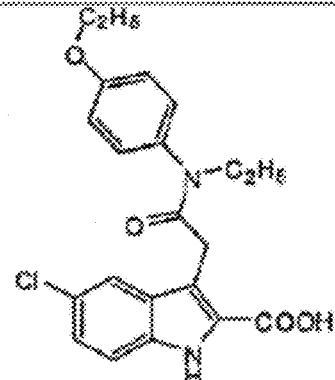
FIG. 10A represents kinetic data measured with various exemplary compounds thought to inhibit GSNOR.
Figure 10A:
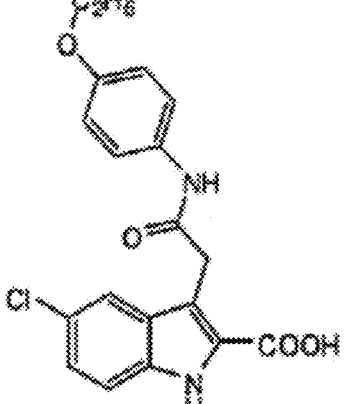
Figure 10A:
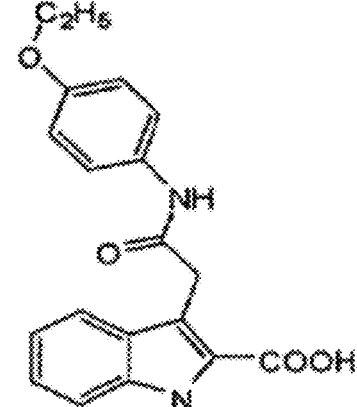
Figure 10E:
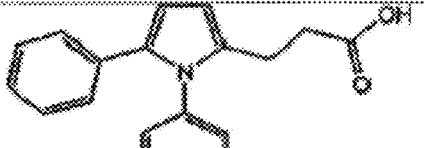
FIG. 10E represents kinetic data measured with various exemplary compounds thought to inhibit GSNOR.
Figure 10E:
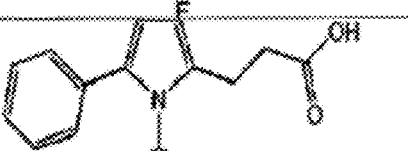
Figure 10E:
Figure 10E:
Figure 10F:
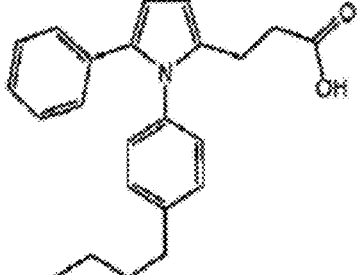
FIG. 10F represents kinetic data measured with various exemplary compounds thought to inhibit GSNOR.
Figure 10F:
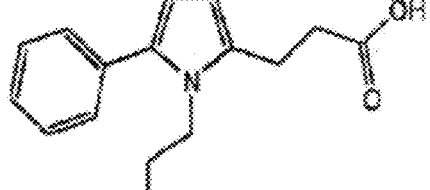
Figure 10F:
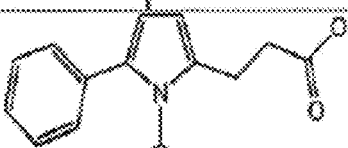
Figure 10F:
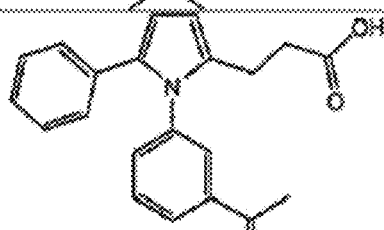
Figure 10F:
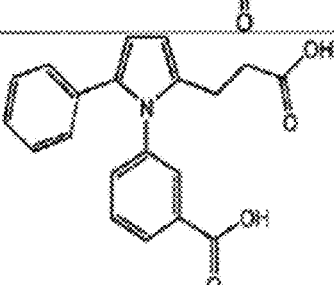
Figure 10G:
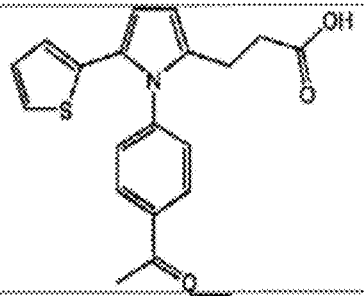
FIG. 10G represents kinetic data measured with various exemplary compounds thought to inhibit GSNOR.
Figure 10G:
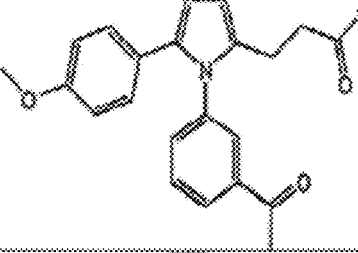
Figure 10G:
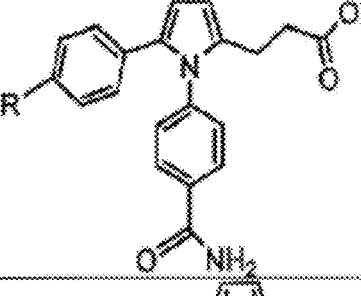
Figure 10G:
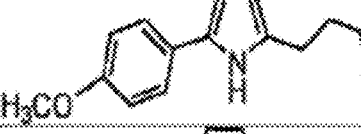
Figure 10G:
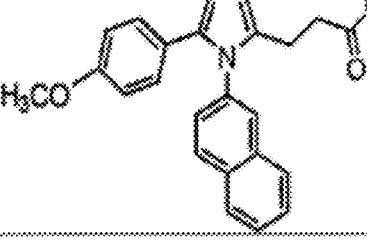
Figure 11:
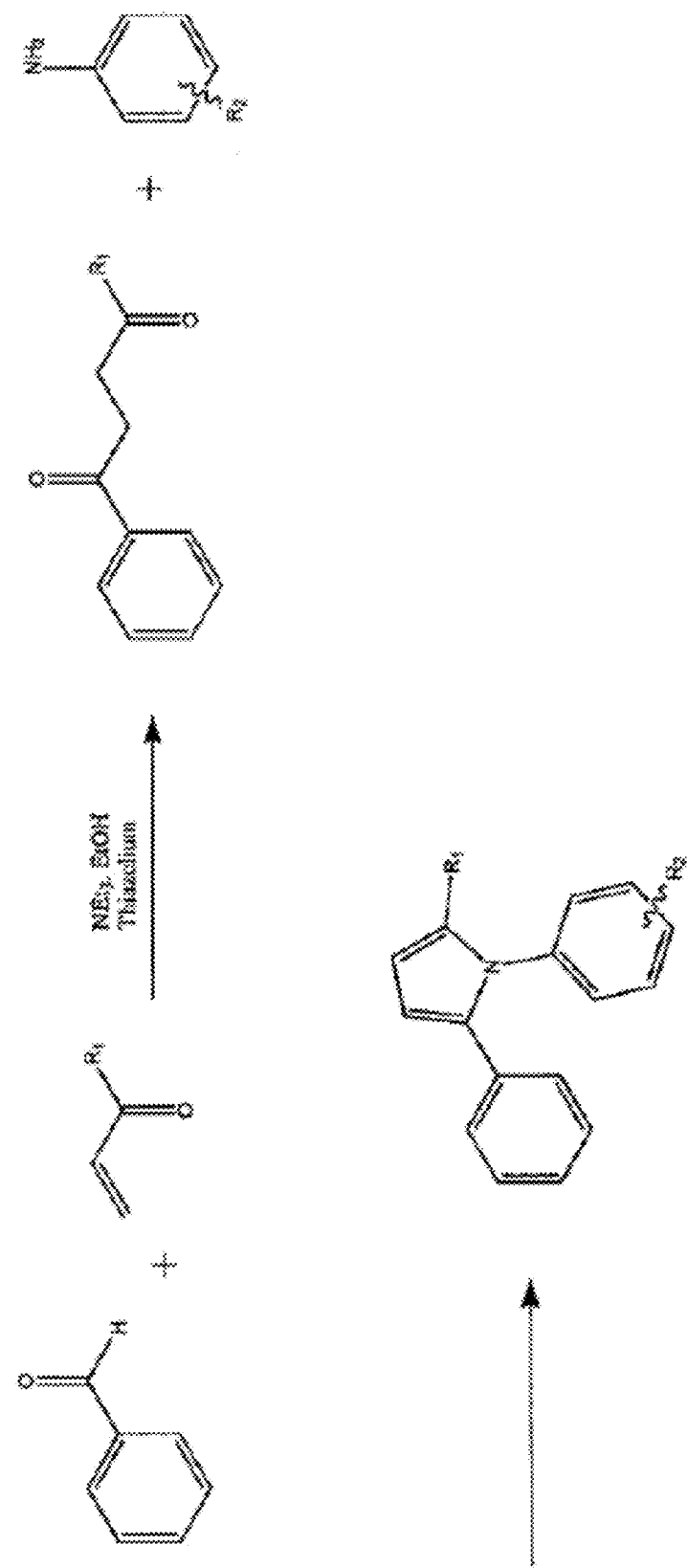
FIG. 11 represents Scheme I of complete synthesis.
Figure 12A:
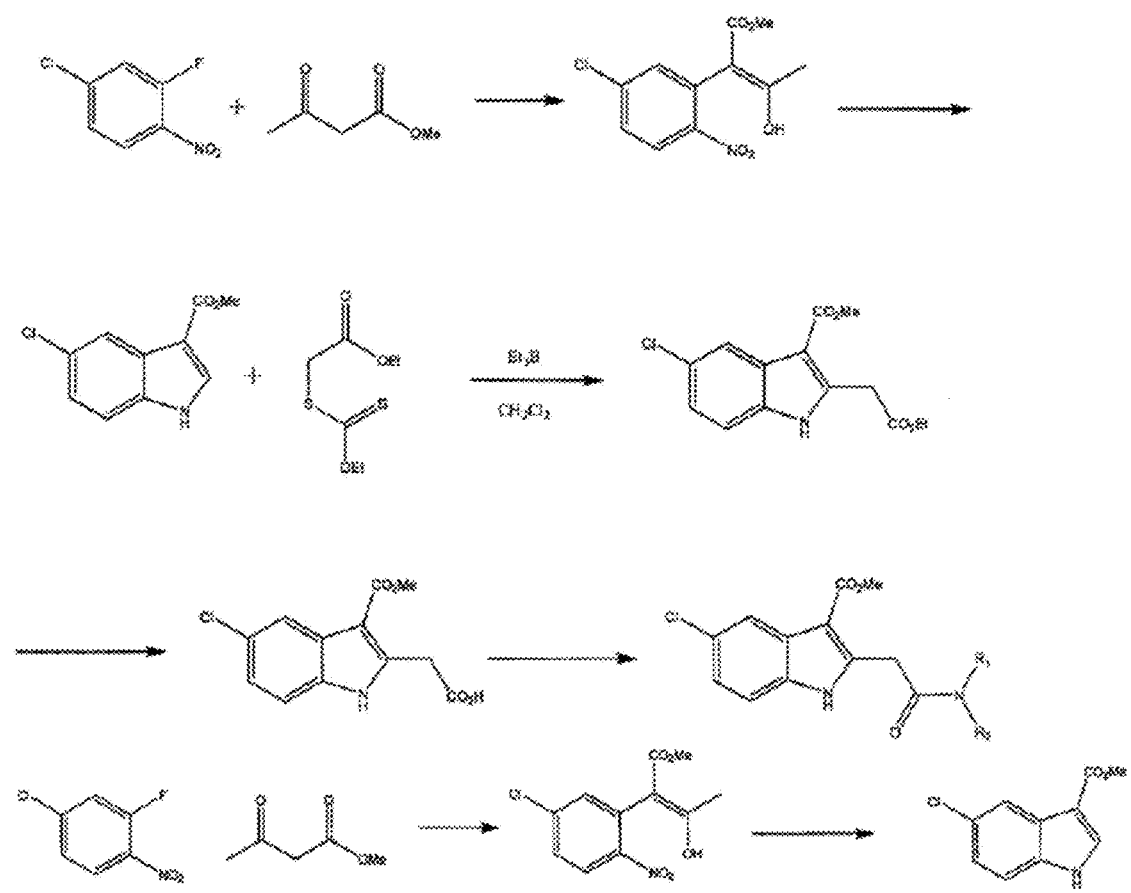
FIG. 12A represents Scheme II of complete synthesis.
Figure 12B:
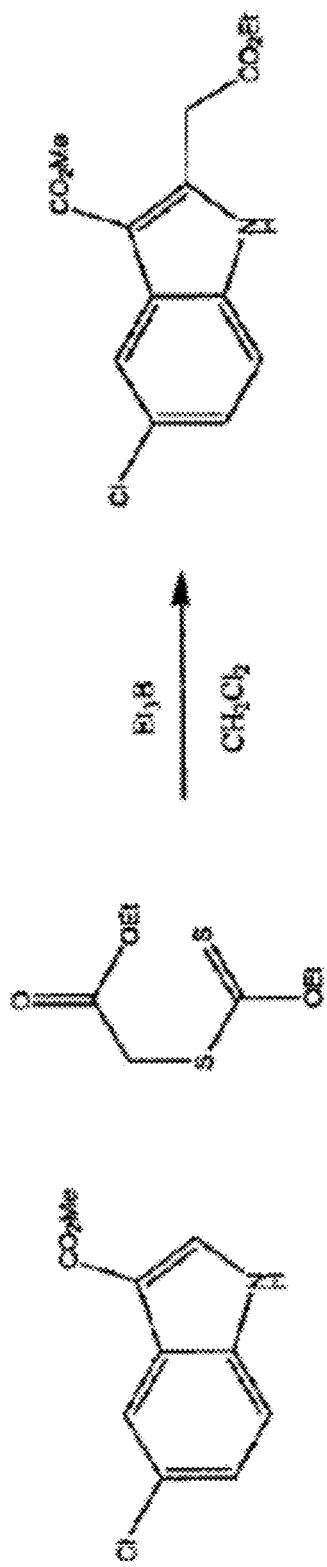
FIG. 12B represents Scheme II of complete synthesis.
Figure 12C:
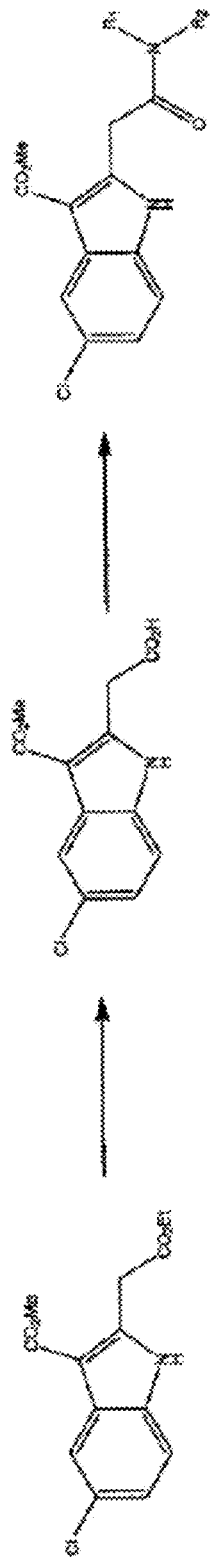
FIG. 12C represents Scheme II of complete synthesis.
Figure 13:
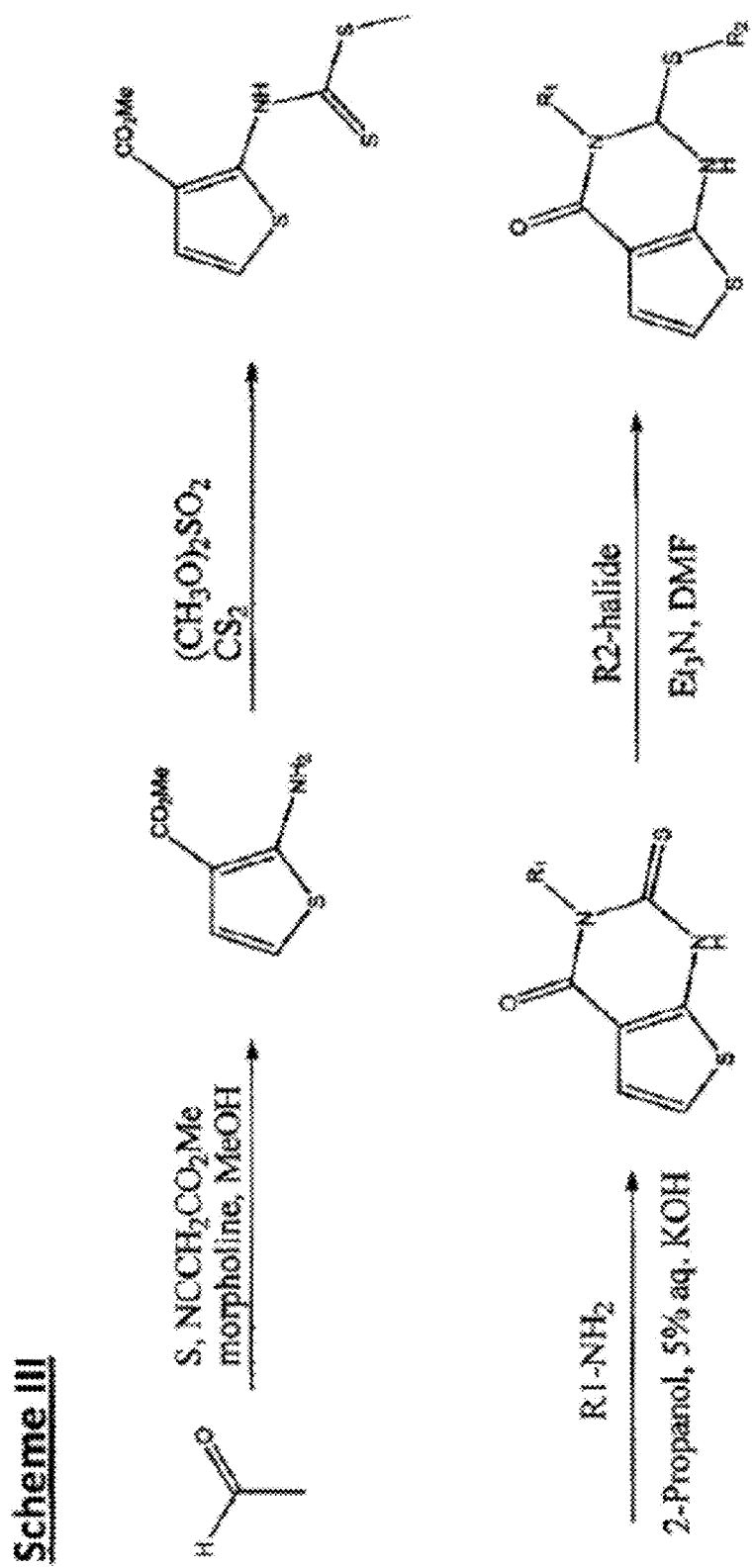
FIG. 13 represents Scheme III of complete synthesis.

The effect of GSNOR inhibition on the nitrosylation of cellular proteins was also examined using the biotin switch assay technique developed by Jaffrey et al [14] and modified by Wang et al [15]. Referring now to FIG. 4, compound 8 increased the nitrosylation of cellular proteins with time in RAW cells. The effects of GSNOR inhibition on the nitrosylation of cellular proteins appeared to peak around 8 hours before decreasing to normal levels within 24 hours. The accumulation of SNOs was less when cells were simultaneously treated with compound 8 and nitric oxide synthase inhibitor, L-NAME (FIG. 4). By way of explanation and not limitations, these results suggest that the accumulation of SNOs in GSNOR inhibited cells occurred from the reaction of constitutively produced nitric oxide (by NOSs) with cellular proteins.

cGMP plays key roles in vascular biology. To test whether inhibition of GSNOR increases cGMP production, RAW 264.7 cells were incubated with 50 µM GSNO±, both with and without compound 8, one of the subject GSNOR inhibitors of this invention. Next the amount of cGMP accumulation after 10 minutes was measured. Referring to FIG. 6, GSNO activates soluble Guanylate Cyclase as previously described (Mayer et al *J Biol Chem*, Vol. 273, Issue 6, 3264-3270, Feb. 6, 1998). Compound 8 (GSNORi in the figure)

potentiates the effect of GSNO by 2.5 fold. Without being limited by any specific explanation, or hypotheses, these results suggest that one mechanism by which compound 8 may exert its biochemical effects is due to its inhibition of GSNOR, which then potentiates the effects of GSNO on cGMP production resulting in higher cGMP levels. These data may explain at a biochemical level the ability of at least some of these compounds that inhibit GSNOR to relax isolated aortic rings as demonstrated elsewhere herein.

Figure 5A:
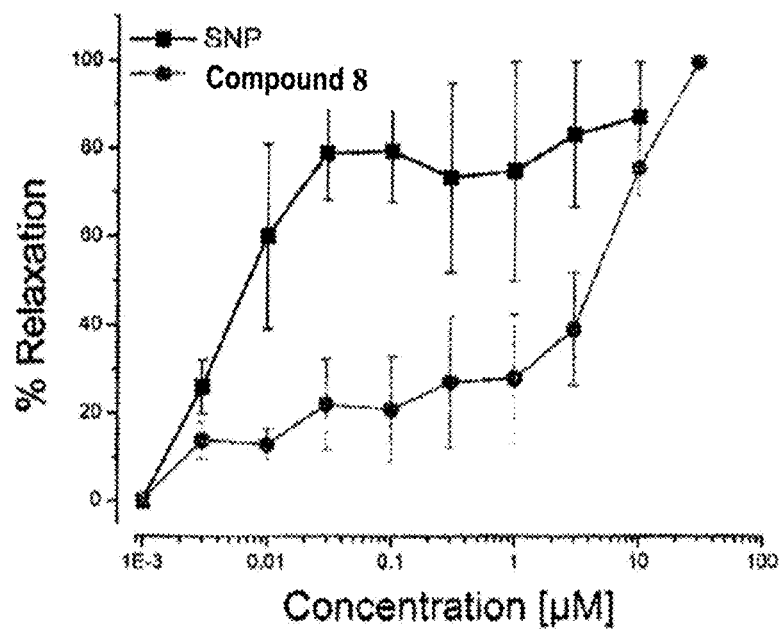
FIG. 5A illustrates a dose-response relationship of compound 8 and sodium nitroprusside.

The increase in the nitrosylation of proteins upon GSNOR inhibition may suggest that GSNOR inhibition should increase the bioactivity of nitric oxide stemming from s-nitrosylation of cellular proteins in organs as well as in cells in tissue culture. We tested this hypothesis by determining the effects of compound 8 on the vascular tone of organ cultures of murine aorta. Compound 8 (50 μM) completely relaxed the vessels within 15 min. A complete concentration response curve revealed an $EC_{50}$ of 5 μM for compound 8 (FIG. 5A), with as little as 300 μM giving ~10% relaxation. Direct comparison with sodium nitroprusside (SNP) revealed that although compound 8 was less potent than SNP at relaxing the vascular smooth muscle (FIG. 5A) and that the relaxation occurred much more slowly, the duration of the effect was much longer than with SNP. The vascular effects of SNP are immediate which explains its clinical utility for hypertensive crises. The GSNORi mediated relaxation took around 3 minutes to begin relaxation but at a 50 μM concentration it sustained vessel relaxation for up to 2 hours, after which the integrity of the vessel preparations begin to decline.

Figure 5B:
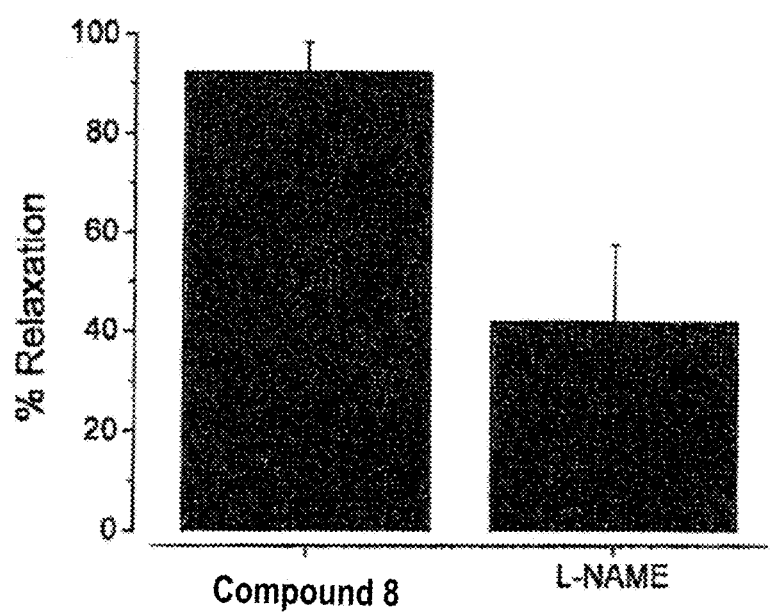
FIG. 5B illustrates the effects of the vasorelaxation to compound 8 with or without the treatment of L-NAME.

Preincubation of aortic rings with 500 μM L-NAME for 30 minutes inhibited the vasorelaxation to compound 8 by roughly 58% (FIG. 5B). The partial inhibition of compound 8 induced relaxation of the aorta by L-NAME suggests that nitric oxide produced by the NOSs is mediating the relaxation of smooth muscles observed during GSNOR inhibition. Thus, GSNOR actively regulates the bioactivity of nitric oxide by regulating the nitrosylation of cellular proteins and confirms the notion that RSNOs are involved in vasorelaxation in an isolated organ.

Therefore, these three compounds help define the cellular effects of inhibiting GSNOR, and potentially harness the beneficial effects of GSNOR inhibition without completely knocking-out its activity.

The accumulation of nitrosothiols by the inhibition of GSNOR are consistent with the studies of Stamler and others illustrating that GSNOR is the primary enzyme involved in regulating levels of s-nitrosylated proteins inside cells. In light of the debate around the sensitivity of the triiodide based quantitation of nitrosothiols, we conclude that GSNOR inhibition, per se would not lead to a large increase in the nitrosylation level of cellular proteins, at least without stimulation of nitric oxide synthases. Without being bound by any specific theory or explanation, these results suggest that partial downmodulation of GSNOR activity, rather than abrogation, may prove the most efficacious. In summary, we report novel inhibitors of s-nitrosoglutathione reductase and many related compounds that inhibit GSNOR perhaps by binding into the GSNO binding site. At least some of these compounds bind to GSNOR at multiple places in the kinetic pathway, thereby affording a type of inhibition not easily overcome by the up-regulation of GSNO and NADH. Data collected using these compounds support the assertion that GSNOR is one of the primary enzymes involved in regulating the nitrosylation of intracellular proteins.

In addition to being structurally diverse, each of the Compounds 6-8 has a free carboxyl group like many of the excellent substrates of GSNOR, including GSNO and 12-hydroxydodecanoic acid. Given the importance of Arg115 at the base of GSNOR active site in the binding of GSNO and HMGSH, it is very likely that the free carboxyl group in Compounds 6-8 is interacting with Arg115. By virtue of not binding in the coenzyme binding site, compounds 6-8 will have a high probability of specifically inhibiting GSNOR among NAD(H) binding dehydrogenases. These compounds may also serve as good lead compounds for obtaining other highly potent cell permeable GSNOR inhibitors.

In order to identify additional compounds that inhibit GSNOR, and may have diagnostic research or therapeutic utility, we tested analogue of specific compounds identified in the original assays. The compounds are disclosed in Table 4. Briefly, compounds 12-14, 43-53, 72, 84, 86 and 72-83 are related to compound 6 of Table 3; compounds 24, 56, 58, 59, 62, 60-62, 64, 66, 67, 69, 70 in table 4 and are related to compound 7 of Table 1.

A number of explanations and experiments are provided by way of explanation and not by limitation. No theory of how the novel technology operates is to be considered limiting, whether proffered by virtue of description, comparison, explanation or example. Accordingly, the following examples and discussion are presented by way of guidance and explanation and not limitation.

EXAMPLES

Materials and Methods

All the chemicals used in the experiments were purchased from Sigma-Aldrich Chemical Company. RAW 264.7 cells, DMEM medium, and fetal bovine serum were purchased from American Tissue and Cell Culture. Recombinant human GSNOR, $\beta_2\beta_2$-, π-, and σ-ADHs were expressed in *E. coli* and purified as described earlier.

Synthesis of Compound 6

Depending upon the substitution pattern, the 1,2-diarylpyrroles reported in this paper were synthesized using the Scheme I. The general synthetic strategy entailed the preparation of suitable 1,4-diketones followed by heating with appropriate amines in the Paal-Knorr condensation, cyclization to yield the targets. The analogs having an alkyl group (R3) Me or Et) at position 5 in the pyrrole ring were synthesized following Scheme 1. The Stetter reaction 16 of substituted benzaldehydes with R,â-unsaturated ketones using the thiazolium salt catalyst proved very versatile and high yielding (NEt3, EtOH, reflux, 60-90%). The condensation of VII with aryl amines (Scheme 1) proceeded smoothly to give good yields (50-80%) of the desired pyrroles. For additional information the reader is directed to see, for example, *Journal of Medical Chemistry*, 1997, Vol. 40. 40, No. 11.

Synthesis of Compound 7

Depending upon the substitution pattern Compound 7 can be syntheses by the general synthesis described in Scheme II. For additional information the reader is directed to see, for example, Trofimov, F. A. et al., *Khimiya Geterotsiklichoskikh Soedinenii*, (10) 1343-6; 1975.

Synthesis of Compound 8

Depending upon the substitution pattern Compound 8 can be syntheses by the general synthesis described in Scheme III. For additional information the reader is directed to see, for example, *J Comb. Chem.* 2004, 6, 573-583.

Figure 3B:
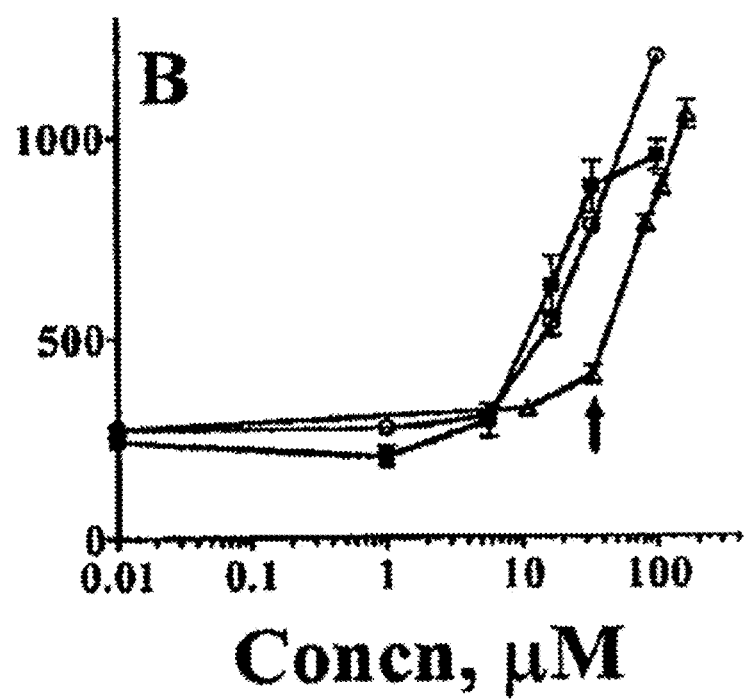
FIG. 3B illustrates the concentration of nitroso species in RAW 264.7 cells in presence of GSNOR inhibitors.

High Throughput Screening:

Referring now to FIG. 3, briefly, RAW 264.7 cells were incubated with 500 μM GSNO alone (γ) or in presence of 33 μM Compound 6 (○) or 7 (Δ) or 8 (■). At indicated times or at 4 hr (in case of B), the cells were lysed and the lysate was analyzed for protein and nitroso species concentration by Bradford and chemiluminescence assay, respectively. For details, see Materials and methods. Data represents mean±SE (n=3–12).

Referring now to FIG. 4, RAW 264.7 cells were cultured in DMEM containing 10% heat-inactivated serum. Cells were treated with 33 µM of Compound 8 for 0, 2, 4, 8, or 24 h alone or in combination with 1 mM NAME for 4 h (lane 4+N). At indicated times, the cells were quenched and the lysate was analyzed for s-nitrosothiol content by the biotin switch assay. Equal amounts of proteins were loaded in each lane and the degree of biotinylation (and hence s-nitrosylation) determined using an anti-biotin antibody.

Referring now to FIG. 5, mouse aorta segments were equilibrated in oxygenated PSS (95% $O_2$ and 5% $CO_2$) at 37° C. Following equilibration, 1 µM phenylephrine was added to each ring for submaximal contraction. After stabilization, increasing concentrations ($10_{-9}$ M to $10_{-4}$ M) of either compound 8 or sodium nitroprusside (SNP) was added to the rings and the tone of the rings determined (B) Inhibition of compound 8 induced relaxation of aortic rings by nitric oxide synthase inhibitor, L-NAME. To pre-equilibrated and submaximally contracted aortic rings with phenylephrine (1 micromolar), LNAME (500 micromolar) was added to the bath and allowed to incubate for 30 minutes. After 30 minutes, compound 8 (50 micromolar) was added and the tone of the rings determined as described above. Each experiment was performed using two rings from three different mice and the mean (±SEM) for each response determined.

Referring now to FIG. 6, RAW 264.7 cells were incubated with 50 µM GSNO±compound 8 the subject GSNOR inhibitor of this invention and then measured the amount of cGMP accumulation after 10 minutes. As shown in the figure GSNO activates soluble Guanylate Cyclase as previously described (Mayer et al *J Biol Chem*, Vol. 273, Issue 6, 3264-3270, Feb. 6, 1998). One mechanism by which compound 8 exerts its biochemical effects is due to its inhibition of GSNOR, which then potentiates the effects of GSNO on cGMP production resulting in higher cGMP levels. These data likely explain at a biochemical level the ability of all these compounds that inhibit GSNOR to relax isolated aortic rings.

Referring now to Table 1, inhibition was studied at pH 10. These assays were performed in 0.1 M sodium glycine containing 1 mM octanol, 1 mM $NAD^+$, 0.1 mM EDTA and 50 µM inhibitor. Inhibition studies at pH 7.5 were performed in 50 mM potassium phosphate pH 7.5 that included 15 µM NADH, 10 µM GSNO, 0.1 mM EDTA and 50 µM inhibitor. The data file to a model consisted with partial inhibition and a hill coefficient of 2.4 in the inhibition curve.

Referring now to Table 2, briefly inhibition studies were performed in presence or absence of about 5 µM inhibitor. These studies were carried out at 25° C. in 50 mM potassium phosphate pH 7.5 including 0.1 mM EDTA. The enzymes activities were measured by following the changes in absorbance at 340 nm. The values show the percent reduction in the enzyme activity (from a minimum of two measurements) caused by the inhibitor. The standard errors for this data are below 15% of the averages shown, except when the inhibition was below 20%. Studies with $\beta_2\beta_2$-, σσ-, π-ADH and involving compounds 5-8 were performed in 0.05% DMSO. Studies with GSNOR were performed in presence of 1% DMSO, except when compound 4 was the inhibitor. Studies with compound 4 were performed in 0.36% DMSO. DMSO at 0.36% inhibited $\beta_2\beta_2$-, σσ-, and π-ADH by 24, 18, and 9%, respectively. Studies with $\beta_2\beta_2$-ADH involved adding 3.5 µg of the enzyme to the assay mixture including 2 mM $NAD^+$, 1 mM ethanol and the inhibitor.

Studies with σσ-ADH involved adding 0.5 µg of enzyme to the assay mixture containing 2 mM $NAD^+$, 30 mM ethanol and the inhibitor. Studies with π-ADH involved adding 19.5 µg of the enzyme to the assay mixture including 1 mM $NAD^+$, 35 mM ethanol and the inhibitor. Studies with GSNOR involved adding 0.1 µg of the enzyme to an assay mixture including 15 µM NADH, 5 µM GSNO and the inhibitor.

Referring now to Table 3, inhibition experiments were performed at 25° C. in 50 mM potassium phosphate (pH 7.5) including 0.1 mM EDTA. A minimum of five concentrations of the varied substrate and three inhibitor concentrations were used for each experiment. NADH and GSNO concentrations were held at 15 or 10 µM, respectively when present as a constant substrate in the assay. The $K_{is}$ and $K_{ii}$ values are respectively the slope and intercept inhibition constants and are listed along with their associated standard errors. All data were fit to a competitive (C), noncompetitive (NC), or uncompetitive (UC) inhibition models. The type of inhibition shown in the table represents the best fit of the data to the given model as judged from F statistics analysis. The $K_D$ value is the equilibrium dissociation constant of the inhibitor for binding to the GSNOR•NADH complex, obtained by measuring the changes in the fluorescence of GSNOR bound NADH with the addition of Inhibitor ($\lambda_{exc}$=350 nm; $\lambda_{emm}$=455 nm). The dissociation constant was measured at 25° C. in 50 mM potassium phosphate pH 7.5. Each $K_D$ value is an average of three independent experiments and is shown with the associated standard error.

The screening for GSNOR inhibitors was performed using a library of 60,000 compounds from ChemDiv Inc in the Chemical Genomics Core facility at Indiana University. Screening was conducted in 384 well plates and involved incubating GSNOR with 12.5 µM compound, 1 mM each of $NAD^+$ and octanol in 0.1 M sodium glycine pH 10. Enzyme activity was determined by measuring the rate of production of NADH spectrophotometrically at 340 nm. Inhibition of GSNOR was calculated from the ratio of enzyme activity in the presence of compounds to that in no compound controls performed on the same assay plate. Following their identification from the high-throughput screening, the GSNOR inhibitory properties of the initial hits were confirmed at the pH 10 using 12-hydroxydodecanoic acid as the substrate and at pH 7.5 using GSNO as the substrate (see the brief description of Table 1 for details on how the assay was carried out.)

Inhibition of ADH Isozymes by Various Compounds:

Inhibition of the $\beta_2\beta_2$-, π-, and σ-ADH was evaluated by determining the inhibitory effect of GSNOR inhibitors on the rate of oxidation of ethanol by each of these ADH isozymes. The assay mixtures included saturating amount of $NAD^+$ (1-2 mM) and ethanol at its $K_M$ concentration for each of the respective enzyme. All the assays were performed at 25° C. in 50 mM potassium phosphate pH 7.5 including 0.1 mM EDTA and involved determining the rate of formation of NADH spectrophotometrically at 340 nm. Specific assay conditions for each isozyme are described in the legend of Table 2.

Dead-End Inhibition Studies:

Inhibition experiments with the GSNOR inhibitors were conducted at 25° C. in 3 ml of 50 mM potassium phosphate (pH 7.5) containing 0.1 mM EDTA. Five different concentrations of GSNO or NADH were used when they were the varied substrates and maintained at 10 and 15 µM, respectively, when present as the nonvaried substrate. A minimum of three inhibitor concentrations were used in these assays and the rate of NADH and GSNO consumption was determined spectrophotometrically by following change in absorbance at 340 nm. The data were fit to the competitive, noncompetitive and uncompetitive inhibition models and the model that the data was chosen on the basis of F-statistics performed using the Graphpad Prizm 4.0 program.

Fluorescence Studies:

Fluorescence studies were conducted in 50 mM potassium phosphate pH 7.5, at room temperature using a Fluoromax-2 fluorescence spectrometer (Instruments S.A., Inc., Edison, N.J.). The equilibrium dissociation constant of GSNOR inhibitors was determined by measuring the changes in the fluorescence of GSNOR bound NADH ($\lambda_{exc}$=350 nm; $\lambda_{emm}$=455 nm) upon the addition of inhibitor. During the experiment, increasing amounts of inhibitor were added to a solution including 2 μM GSNOR and 1.7 μM NADH. The decrease in fluorescence at 455 nm with each addition of inhibitor was plotted against the final concentration of inhibitor and the data were fitted to equation 1 using nonlinear regression to obtain the dissociation constant of the inhibitor for GSNOR-NADH complex, $$\Delta F = \Delta F_M \frac{([L_T] + [E_T] + K_D) - \sqrt{([L_T] + [E_T] + K_D)^2 - 4[L_T][E_T]}}{2[E_T]} \quad (1)$$

In equation 1, ΔF is the change in the fluorescence at 455 nm upon the addition of inhibitor. $\Delta F_M$ is the maximum fluorescence change that was obtained from curve fitting. $E_T$ and $L_T$, are the concentrations of GSNOR and inhibitor, respectively. $K_D$ is the equilibrium dissociation constant for the formation of GSNOR•NADH•Inhibitor complex. The data were fitted using the Graphpad Prizm 4.0.

Cell Culture Studies:

RAW 264.7 cells were cultured in DMEM medium supplemented with 10% FBS, 200 U/ml of penicillin and 200 μg/mL of streptomycin. The cells were incubated at 37° C. in an atmosphere containing 5% $CO_2$ and 95% air. For the experiments, 1-2×10$^6$ cells were plated in six-well plates a day before the experiment. On the day of the assay the medium was replaced with 3 ml of fresh medium and the cells were treated with compounds for a predetermined length of time. Following the incubation period, the cells were washed three times with PBS and scraped off the plate in 250 μl of lysis buffer (50 mM potassium phosphate pH 7.0 containing 50 mM NEM and 1 mM EDTA). Cells were lysed by sonication using a micro tip probe (three pulses of 30% duty cycle; 2 output control on a Fisher Sonicator). Cell debris was pelleted by centrifugation (10 min at 16,000 g) and the cell lysate was analyzed for protein concentration using the Bio-Rad dye-binding protein assay. The concentration of nitroso compounds in the cell lysate was determined using the triiodide based chemiluminescence method using a Sievers 280 nitric oxide analyzer. Briefly, cell lysates were treated with 15% v/v of a sulfanilamide solution (5% w/v in 0.2 M HCl) and kept at room temperature for 5 min to remove nitrite. The triiodide mixture was prepared fresh every day as described earlier and kept at 60° C. in the reaction vessel. The concentration of nitroso species was derived from a standard curve generated using GSNO. For determining the amount of the small size nitroso compounds in the cell lysate, a 5 kDa-cutoff Amicon ultra filtration unit was used according to the supplier's instructions. The amount of s-nitrosothiols in the cell lysate was determined by treating initially passing the cell lysate through a microspin column and treating the eluate with 5 mM $HgCl_2$ before determining the nitroso compound concentration using chemiluminescence. For some experiments the cells were pretreated with the compounds for 16 hours prior to the day of experiment. Later experiments showed that this pretreatment had no effect on the rate of accumulation of nitroso species inside the cells.

Determination s-Nitrosothiol Accumulation in RAW 264.7 Cells Using the Biotin Switch Assay Method:

RAW 264.7 cells were cultured in 10% heat-inactivated serum containing DMEM. Cells were treated with 33 micromolar compound 8 for varied lengths of time alone or in combination with 1 mM NAME for 4 h (4+N). At indicated times, the cells were quenched and the lysate was analyzed for s-nitrosothiol content by the biotin switch assay as described by Jaffrey et al [1] with modifications suggested by Wang et al [2] and Zhang et al [3]. Briefly, free sulfydryls in ~200 μg of cell lysate were blocked with 20 mM MMTS in 1 ml of HEN buffer (250 mM HEPES pH 7.7 containing 1 mM EDTA and 0.1 mM Neocuproníne) containing 2% SDS at 50° C. for 20 min. Free MMTS was removed by gel-filtration spin columns and the blocked proteins were labeled with 1 mM Biotin-HPDP (Pierce) in presence or absence of 30 mM ascorbate and 2 μM CuCl for 2.5 hours. Equal amounts of proteins were loaded in each lane and the degree of biotinylation (and hence s-nitrosylation) determined using an anti-biotin antibody (SIGMA).

Wire Myography:

Mice were anesthetized with diethyl ether. A thoracotomy was performed to expose thoracic and abdominal aorta. A 25 gauge syringe was inserted into the apex of left ventricle and perfused free of blood with oxygenated Krebs Henseleit buffer. The right atrium was cut to provide an exit for blood. The aorta was removed and cleaned of fat and adventitia. The aorta was cut into 2-mm-long segments and mounted on a four-channel wire myograph (AD Instruments). Vessel rings were maintained in 10-ml organ baths with oxygenated PSS (95% $O_2$ and 5% $CO_2$) at 37° C. Rings were allowed to equilibrate for 80 minutes with the buffer in each organ bath changed every 20 min. One gram pretension was placed on each aortic ring (appropriate starting tension for optimal vasomotor function as determined in previous experiments). An eight-channel octal bridge (Powerlab) and data-acquisition software (Chart version 5.2.2) were used to record all force measurements. After equilibration for 80 min, 1 μM 27 phenylephrine was added to each ring for submaximal contraction. After stabilization, either compound 8 or sodium nitroprusside (SNP) was added to the rings and the tone of the rings determined. For the determination of SNP and ACh dose-response relationships, aortic rings were precontracted with $10_{-6}$ M PE, and SNP or compound 8 was then added in increasing concentrations from $10_{-9}$ M to $10_{-4}$ M. In a subset of experiments, L-NAME was added (500 μM final) to the bath and allowed to incubate for 30 minutes. After 30 minutes, compound 8 was added and the tone of the rings determined as described above.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the novel technology. All patents, patent applications, and references to texts, scientific treatises, publications, and the like referenced in this application are incorporated herein by reference in their entirety.

What is claimed is:

1. A method of treating an inflammatory disease associated with GSNOR activity, comprising the steps of:
administering to a patient in need thereof a therapeutically effective dose of a compound having a structure:

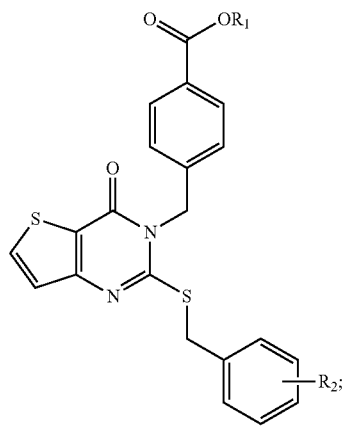

R₁ = —H, —CH₃, —C₂H₅, —C₃H₇
R₂ = —H, —CN, —OH, —CH₂OH or pharmaceutically acceptable salt or ester thereof, wherein said inflammatory disease associated with GSNOR activity is selected from the group consisting of: asthma, idiopathic pulmonary fibrosis, chronic obstructive pulmonary disease, lung disease due to cystic fibrosis, cystic fibrosis, ulcerative colitis and Crohn's disease.

2. The method according to claim 1, wherein the therapeutically effective amount of said compound is in the range of about 0.01 mg/kg per of body mass day to about 1000 mg/kg of body mass per day.

3. The method of claim 1, wherein the compound is

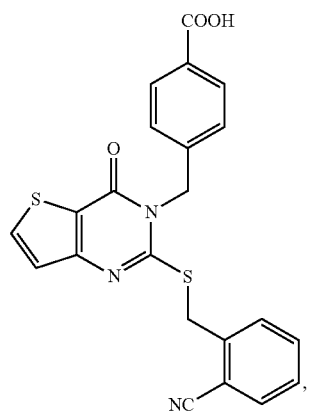 [SMILES: N#Cc1ccccc1CSc1nc2ccsc2c(=O)n1Cc1ccc(C(=O)O)cc1]

or a pharmaceutically acceptable salt or ester thereof.

4. The method of claim 3, wherein the inflammatory disease is selected from the group of diseases of the lung consisting of: asthma, chronic obstructive pulmonary disease, idiopathic pulmonary fibrosis and cystic fibrosis.

* * * * *